United States Patent
Ogura et al.

(10) Patent No.: US 12,159,365 B2
(45) Date of Patent: Dec. 3, 2024

(54) IMAGE PROCESSING APPARATUS, IMAGE PROCESSING METHOD, AND PROGRAM

(71) Applicant: Sony Group Corporation, Tokyo (JP)

(72) Inventors: Sho Ogura, Tokyo (JP); Yuya Yamashita, Tokyo (JP)

(73) Assignee: Sony Group Corporation, Tokyo (JP)

( * ) Notice: Subject to any disclaimer, the term of this patent is extended or adjusted under 35 U.S.C. 154(b) by 45 days.

(21) Appl. No.: 17/434,825

(22) PCT Filed: Mar. 13, 2020

(86) PCT No.: PCT/JP2020/011047
§ 371 (c)(1),
(2) Date: Aug. 30, 2021

(87) PCT Pub. No.: WO2020/203167
PCT Pub. Date: Oct. 8, 2020

(65) Prior Publication Data
US 2022/0148128 A1 May 12, 2022

(30) Foreign Application Priority Data
Mar. 29, 2019 (JP) .................. 2019-065814

(51) Int. Cl.
*G06T 3/16* (2024.01)
*G06F 3/0484* (2022.01)
(Continued)

(52) U.S. Cl.
CPC .............. *G06T 3/16* (2024.01); *G06F 3/0484* (2013.01); *G06T 3/20* (2013.01); *G06T 11/00* (2013.01); *G06T 2200/24* (2013.01)

(58) Field of Classification Search
CPC ......... G06T 3/0087; G06T 3/20; G06T 11/00; G06T 2200/24; G06F 3/0484
See application file for complete search history.

(56) References Cited

U.S. PATENT DOCUMENTS

2017/0142486 A1* 5/2017 Masuda .................. H04N 23/69
2018/0150989 A1* 5/2018 Mitsui .............. H04N 5/232935
(Continued)

FOREIGN PATENT DOCUMENTS

| JP | 2016-194784 A | 11/2016 |
|---|---|---|
| JP | 2018-139102 A | 9/2018 |
| WO | WO 2018/235608 A1 | 12/2018 |

OTHER PUBLICATIONS

International Search Report issued Jun. 9, 2020 in PCT/JP2020/011047 filed Mar. 13, 2020, 2 pages.

*Primary Examiner* — William A Beutel
(74) *Attorney, Agent, or Firm* — Oblon, McClelland, Maier & Neustadt, L.L.P.

(57) ABSTRACT

Combined use of a recommended viewpoint and a free viewpoint is achieved without display of a position of the recommended viewpoint using a frame or the like. A detection unit detects a viewpoint position change instruction. An output unit outputs a part of an image to a display unit. In this case, an output range (an image range corresponding to a current viewpoint) is changed according to a viewpoint position change unit instruction after output of a recommended range such that the output range transits in a direction toward the recommended range on the basis of a predetermined condition. For example, the predetermined condition is deviation of the output range from the recommended range. Moreover, for example, a transition speed is controlled such that return to the recommended range is achieved faster as a positional difference between the output range and the recommended range becomes larger.

18 Claims, 22 Drawing Sheets

(51) Int. Cl.
  *G06T 3/20* (2006.01)
  *G06T 11/00* (2006.01)

(56) References Cited

U.S. PATENT DOCUMENTS

2018/0165830 A1* 6/2018 Danieau ................. G06F 3/012
2018/0307398 A1* 10/2018 Kim .................... G06F 3/04815
2019/0132569 A1* 5/2019 Karpenko ........... G06F 3/04886
2020/0137375 A1* 4/2020 Kroon ................. H04N 13/302

* cited by examiner

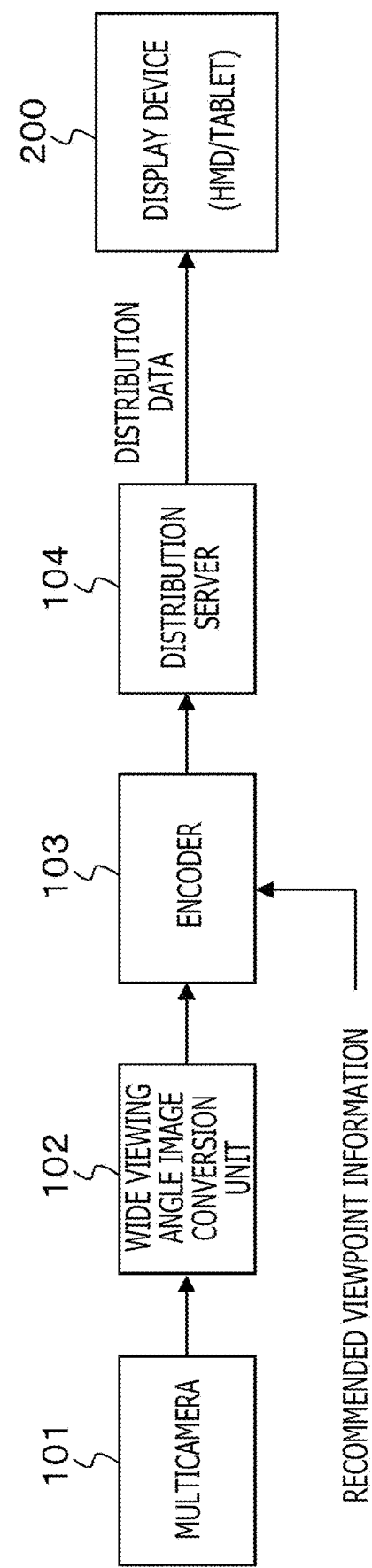

FIG. 4
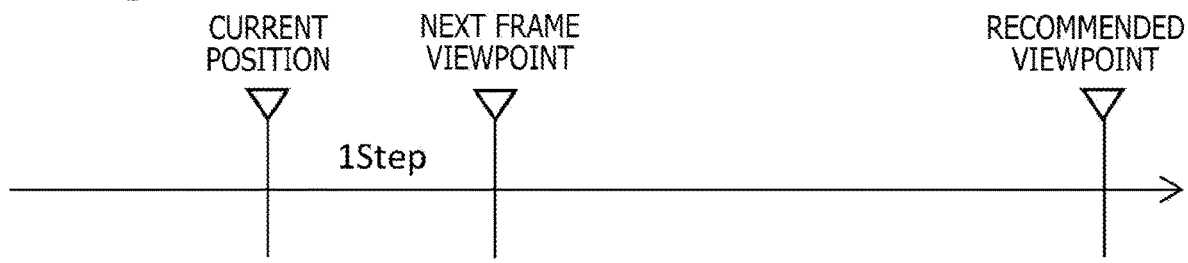
FIG. 5
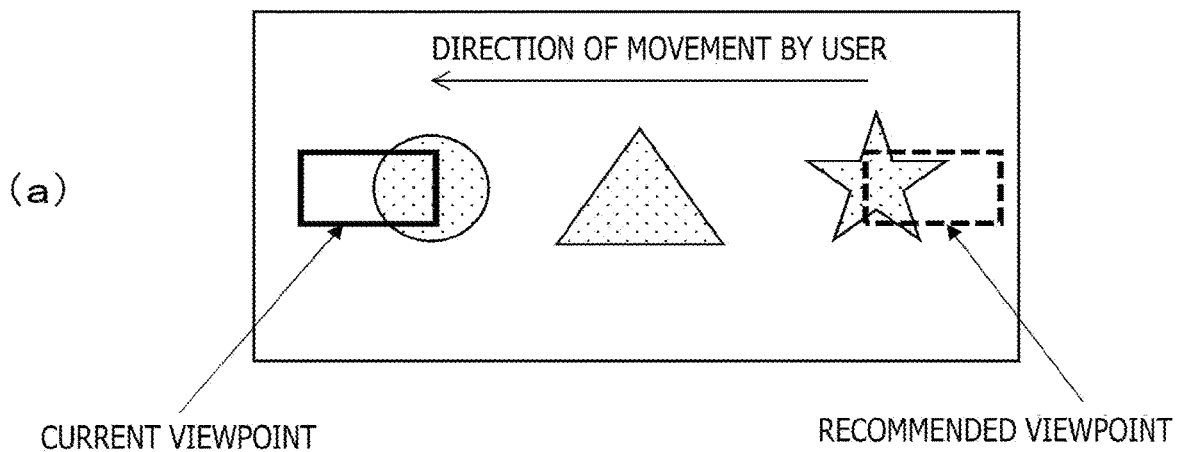
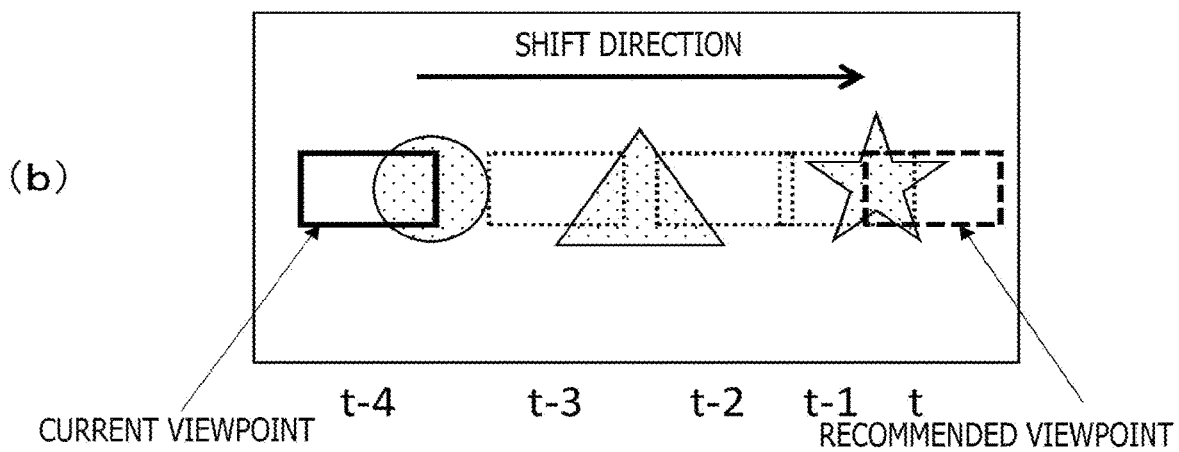

FIG. 6
(a) PROJECTION IMAGE
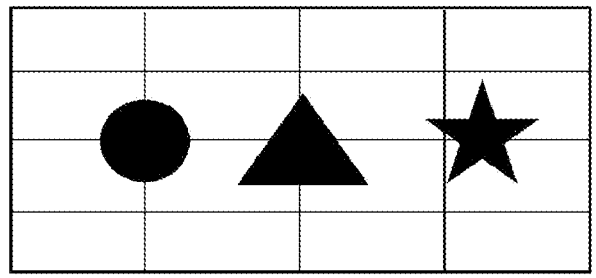
(b) PROJECTION IMAGE
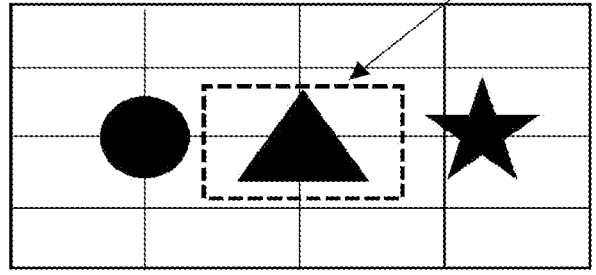
VIEWPOINT POSITION RANGE
(c) DISPLAY IMAGE
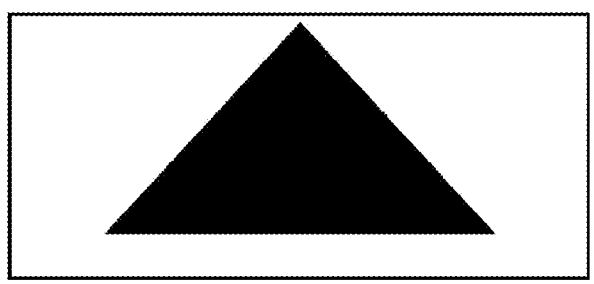

FIG. 14
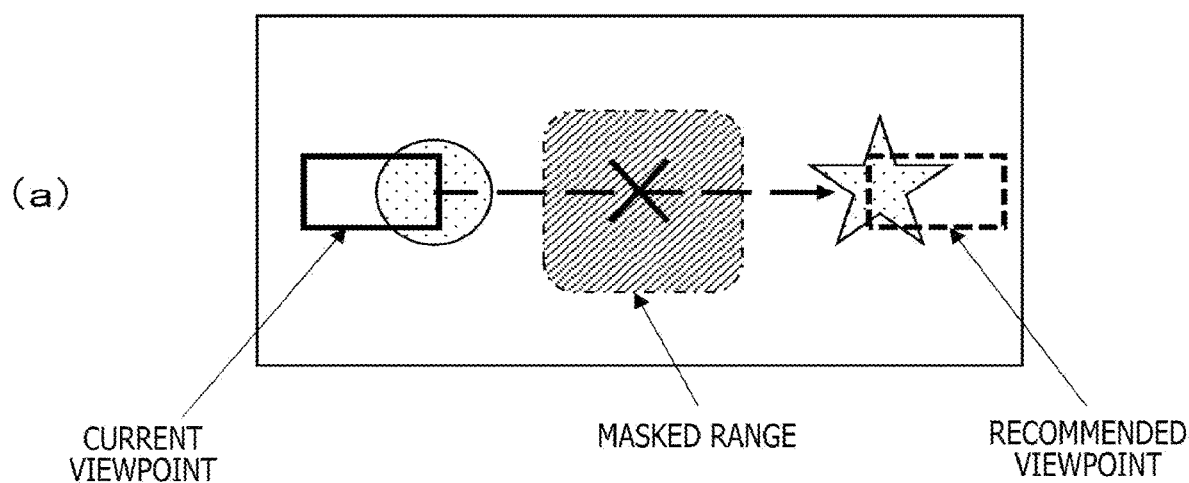
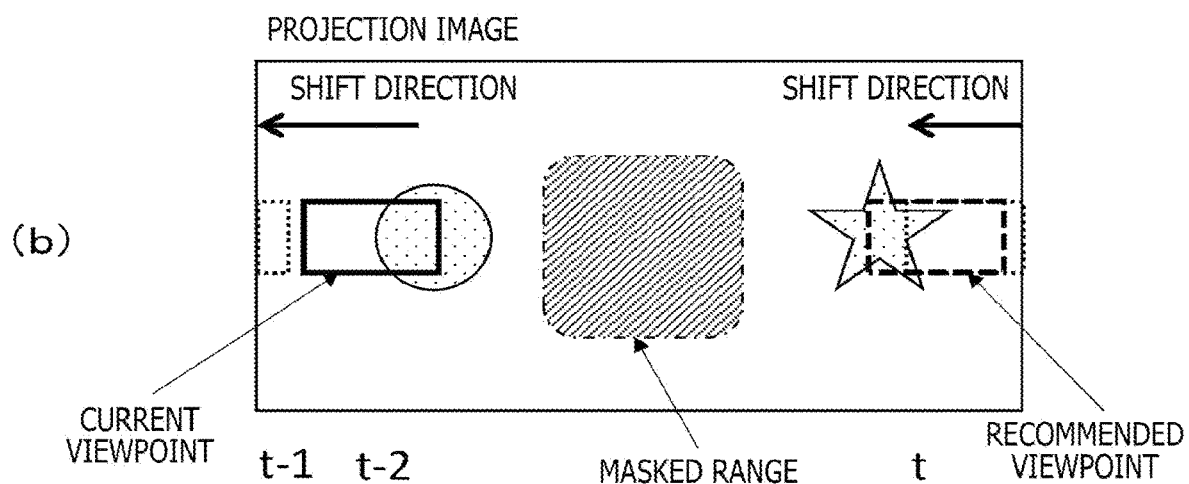

F I G . 1 6
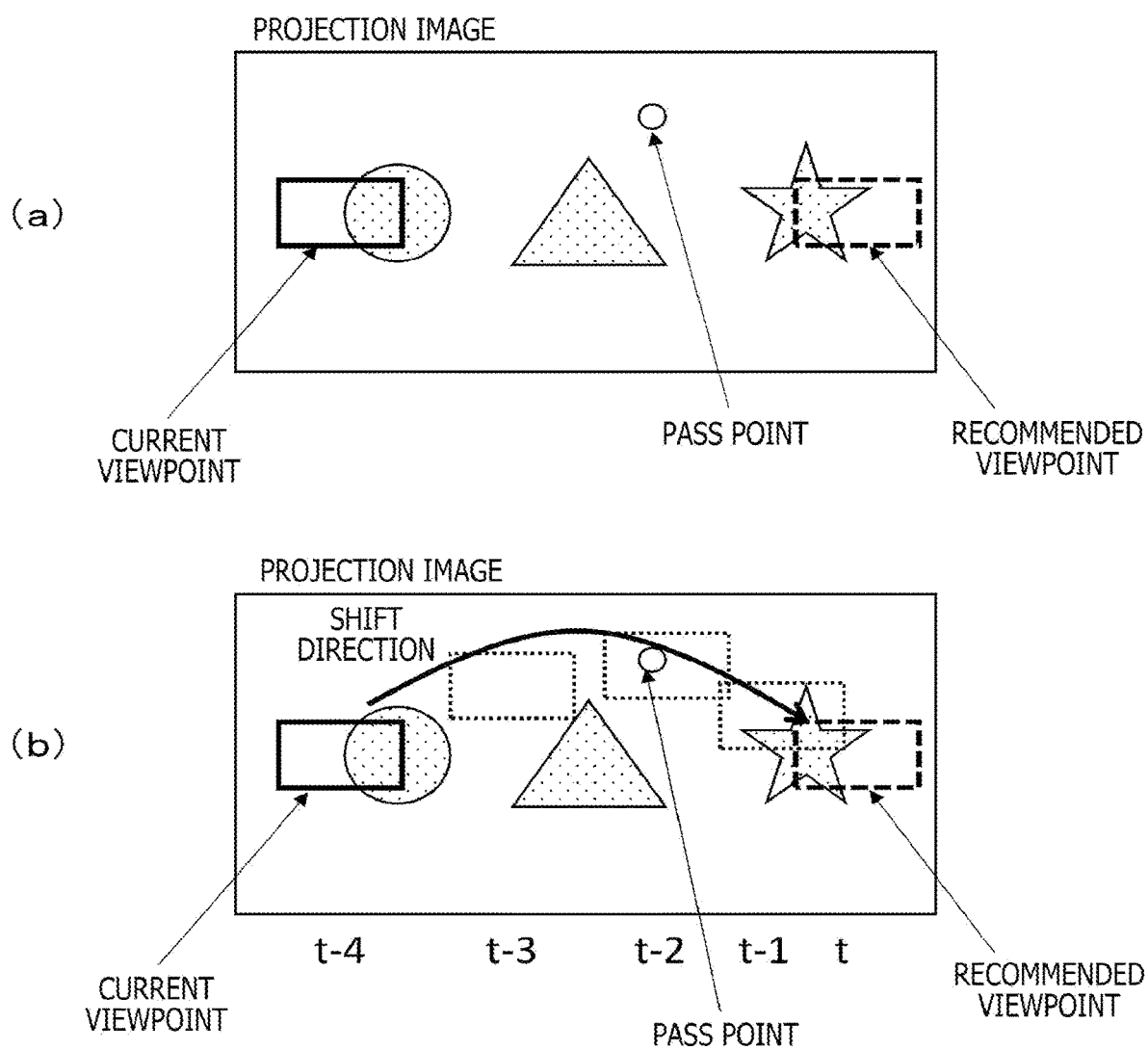

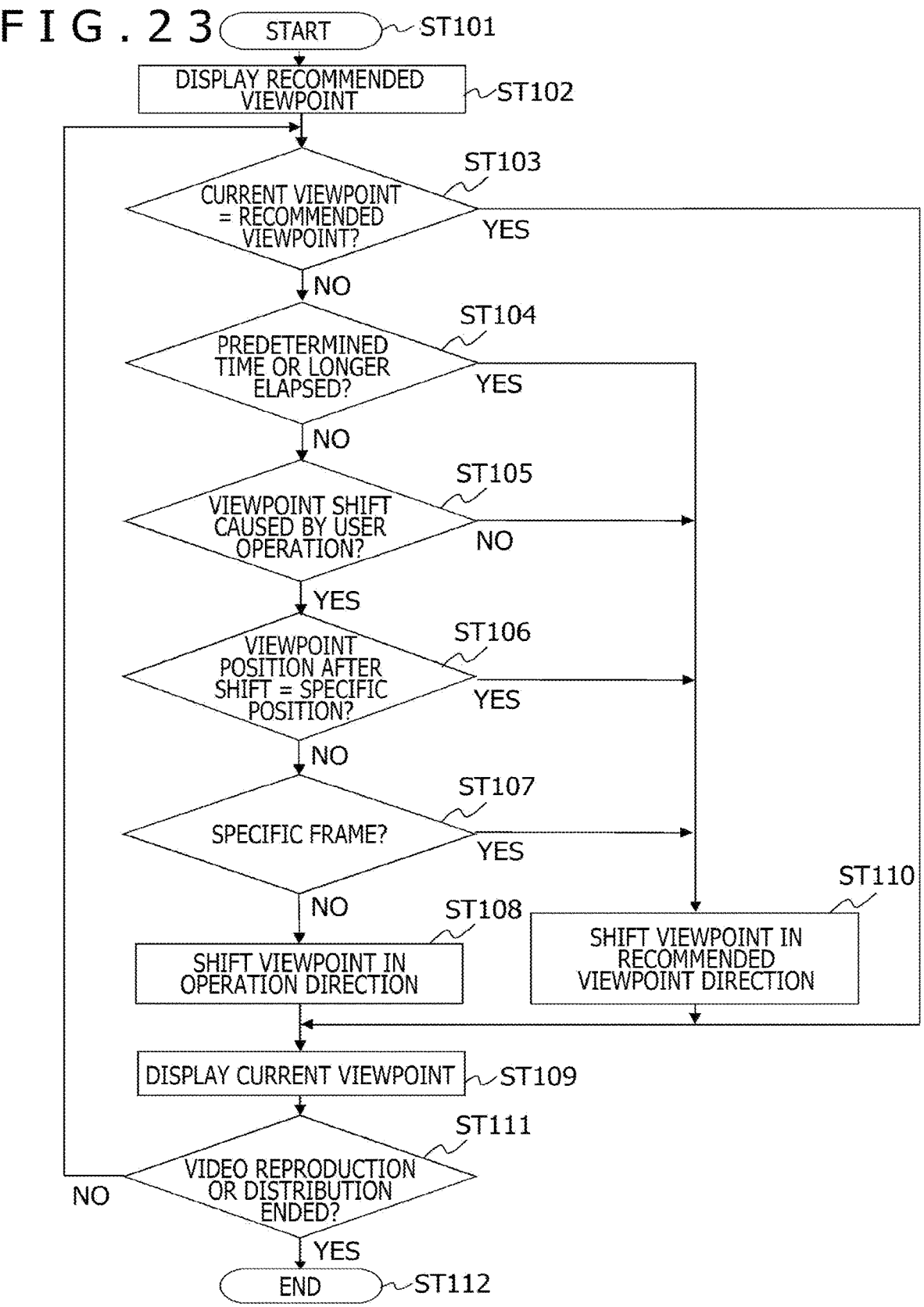

IMAGE PROCESSING APPARATUS, IMAGE PROCESSING METHOD, AND PROGRAM

TECHNICAL FIELD

The present technology relates to an image processing apparatus, an image processing method, and a program, and particularly to an image processing apparatus and the like capable of offering preferable observation of a wide viewing angle image, such as a VR image and a panorama image, for a user.

BACKGROUND ART

A method for transmitting recommended viewpoint information together with wide viewing angle image data having an angle of view of 360° or smaller has been defined under OMAF (Omnidirectional Media Application Format) standards of MPEG-DASH (Dynamic Adaptive Streaming over HTTP). Moreover, PTL 1 contains description about recommended viewpoint display, for example.

CITATION LIST

Patent Literature

[PTL 1]
JP 2016-194784 A

SUMMARY

Technical Problem

During display of a recommended viewpoint, only this recommended viewpoint is viewable in a wide viewing angle image. On the other hand, a recommended viewpoint position is difficult to recognize in a freely viewable state. In this case, it may be considered to display a recommended viewpoint using a frame or the like. However, this display may produce such inconvenience that interpretation of the world in the image collapses at the corresponding portion.

An object of the present technology is to achieve combined use of a recommended viewpoint and a free viewpoint without display of a position of the recommended viewpoint using a frame or the like.

Solution to Problem

A concept of the present technology is directed to an image processing apparatus including: a detection unit that detects viewpoint shift information according to a viewpoint position change instruction; an output range determination unit that determines an output range of an image containing recommended viewpoint information on the basis of the recommended viewpoint information and the viewpoint shift information; and an output unit that outputs a part of the image to a display unit as a display image on the basis of the determined output range. The output range determination unit determines the output range such that the display image lies within a recommended range indicated by the recommended viewpoint information in a case where the display image meets a predetermined condition.

According to the present technology, the detection unit detects viewpoint shift information according to a viewpoint position change instruction. The viewpoint position change instruction is given by a gyro sensor (angular speed sensor), a user operation, or the like, for example. The output range determination unit determines an output range of an image containing recommended viewpoint information on the basis of the recommended viewpoint information and the viewpoint shift information. In addition, the output unit outputs a part of the image to the display unit as a display image on the basis of the determined output range. For example, the image is a wide viewing angle image such as a VR image and a panorama image. The output range determination unit determines the output range such that the display image lies within a recommended range indicated by the recommended viewpoint information in a case where the display image meets the predetermined condition. For example, the output range determination unit may determine the output range such that the display image transits in a direction toward the recommended range.

Moreover, for example, the predetermined condition may include a case where the display image is different from the recommended range. Furthermore, for example, the predetermined condition may include a case where the display image is different from the recommended range for a predetermined time or longer. In addition, for example, the predetermined condition may additionally include a case where the viewpoint shift information is not detected.

Moreover, for example, the predetermined condition may include a case where the display image lies within a specific range in the image. Further, for example, the predetermined condition may include a case where the display image is different from the recommended range in a state where the image is contained in an image of a specific frame. In addition, for example, the predetermined condition may include a case where the display image is different from the recommended range and besides an instruction of transition to the recommended range is issued as the viewpoint shift information.

Moreover, for example, the output range determination unit may control a speed of the transition on the basis of a positional difference between the display image and the recommended range such that the speed of the transition becomes higher in a case where the positional difference is large than in a case where the positional difference is small. Further, for example, the output range determination unit may control a speed of the transition such that return to the recommended range is achieved within a certain time. In addition, for example, the output range determination unit may control a speed of the transition such that return to the recommended range is achieved at a certain speed.

Moreover, for example, the output range determination unit may interpolate a route of the transition by spherical linear interpolation. Further, for example, the output range determination unit may interpolate a route of the transition by linear interpolation.

Moreover, for example, in a case where the display image is different from the recommended range as a result of a change of a viewpoint position based on the viewpoint shift information, the output range determination unit may determine the output range such that a current output range shifts along a route in a direction opposite to a viewpoint position change direction corresponding to the viewpoint position change instruction at the time of the transition. Further, for example, the output range determination unit may determine the output range such that a shift is achieved along a shortest route to the recommended range from the display image at the time of the transition.

Moreover, for example, in a case where the image contains masked range information indicating a masked range, the output range determination unit may determine the output range such that a shift is achieved along a route not passing through the masked range at the time of the transition. Further, for example, in a case where the image contains pass point information indicating a pass point, the output range determination unit may determine the output range such that a shift is achieved along a route passing through the pass point at the time of the transition.

Moreover, for example, in a case where recommended point information contains a plurality of recommended ranges, the output range determination unit may determine the output range such that a shift is achieved toward a recommended range located at a position closest to the display image in the plurality of recommended ranges, or toward a recommended range located at a position selected by a user at the time of the transition.

As described above, the present technology determines an output range of an image containing recommended viewpoint information on the basis of the recommended point information and the viewpoint shift information. Accordingly, combined use of a recommended viewpoint and a free viewpoint is achievable without display of a position of the recommended viewpoint using a frame or the like.

BRIEF DESCRIPTION OF DRAWINGS

FIG. 1 is a block diagram depicting a configuration example of an image distribution system according to an embodiment.

FIG. 4 is a diagram for explaining a process performed by a transition calculation unit for obtaining a viewpoint position of a next frame.

FIG. 5 is a diagram for explaining transition from a current viewpoint to a recommended viewpoint.

FIG. 6 is a diagram for explaining cutting and displaying an image corresponding to a current viewpoint.

FIG. 14 is a diagram for explaining a case where a masked range is present in a direction opposite to a direction corresponding to movement caused by a user at the time of transition from a current viewpoint to a recommended viewpoint.

FIG. 16 is a diagram for explaining a case where a pass point is set at the time of transition from a current viewpoint to a recommended viewpoint.

FIG. 23 is a flowchart presenting an example of a display processing procedure performed by the display device.

DESCRIPTION OF EMBODIMENT

Figure 2:
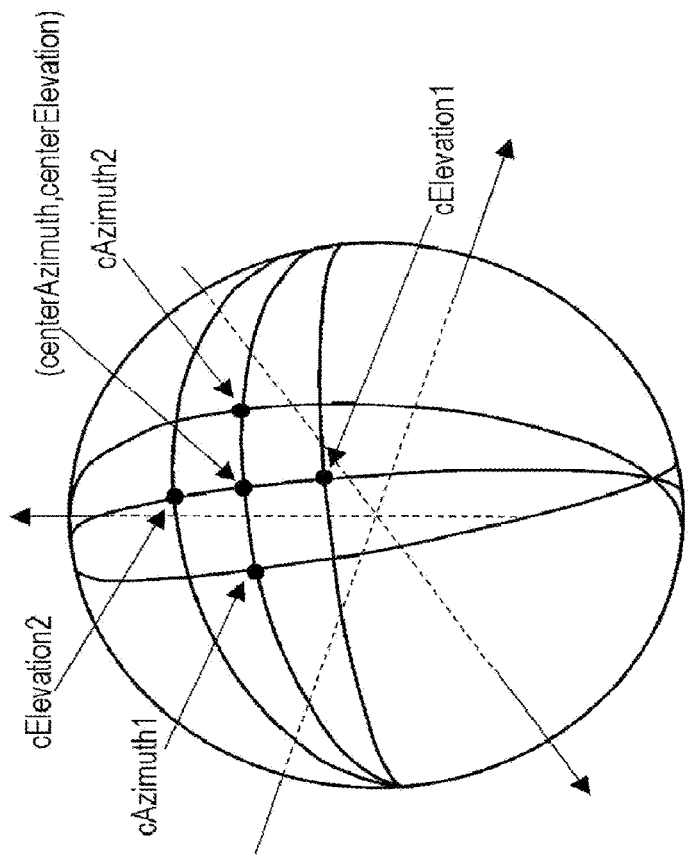
FIG. 2 is a diagram for explaining recommended viewpoint information and others.

A mode for carrying out the invention (hereinafter referred to as an "embodiment") will be hereinafter described. Note that the description will be presented in a following order.
1. Embodiment
2. Application
3. Modification 1. Embodiment

[Image Distribution System]

FIG. 1 depicts a configuration example of an image distribution system 10 according to an embodiment. The image distribution system 10 includes a distribution side device, and a display device 200 functioning as a reception side device. Possible examples of the display device 200 include an HMD (Head Mounted Display) and a tablet.

The distribution side device includes a multicamera 101, a wide viewing angle image conversion unit 102, an encoder 103, and a distribution server 104.

The multicamera 101 obtains image data of a spherical captured image. For example, the multicamera 101 performs imaging by a back-to-back method using two cameras to obtain wide viewing angle front and rear images each having a viewing angle of 180° or larger and captured using a fish-eye lens as a spherical captured image.

The wide viewing angle image conversion unit 102 performs flat packing of a spherical captured image obtained by the multicamera 101 to obtain a rectangular projection image (Projection picture). This projection image is an image corresponding to a wide viewing angle image which has an angle of view of 360° or smaller. In this case, an equirectangular format or the like is selected as a format type of the projection image, for example. Note that the wide viewing angle image conversion unit 102 scales the projection image as necessary to obtain a projection image having a predetermined resolution.

The encoder 103 performs HEVC or other coding, for example, for image data of the projection image received from the wide viewing angle image conversion unit 102 to obtain coded image data, and generates a video stream containing this coded image data. In this stage, the encoder 103 inserts recommended viewpoint information into the video stream for each frame of the video stream.

The recommended viewpoint is automatically set within a range containing a performer estimated by a position sensor or image recognition, for example, or set within a range manually designated by a director, for example. The recommended viewpoint set herein is not limited to only one point, but may be set at a plurality of points.

FIG. 2(a) depicts a spherical surface corresponding to a spherical captured image. FIG. 2(b) schematically depicts a rectangular projection image in a case where an equirectangular format type is adopted. A center of this projection image is located at (0, 0).

For example, as depicted in FIG. 2(c), recommended viewpoint information includes a frame number, central angle information, horizontal angle information, vertical angle information, a recommended viewpoint number, and others. The central angle information, the horizontal angle information, and the vertical angle information are each angle information associated with a spherical captured image (see FIG. 2(a)).

Returning to FIG. 1, the distribution server 104 transmits a video stream generated by the encoder 103 to the display device 200 as distribution data. Note that this distribution may be achieved either by broadcasting or by communication.

Figure 3:
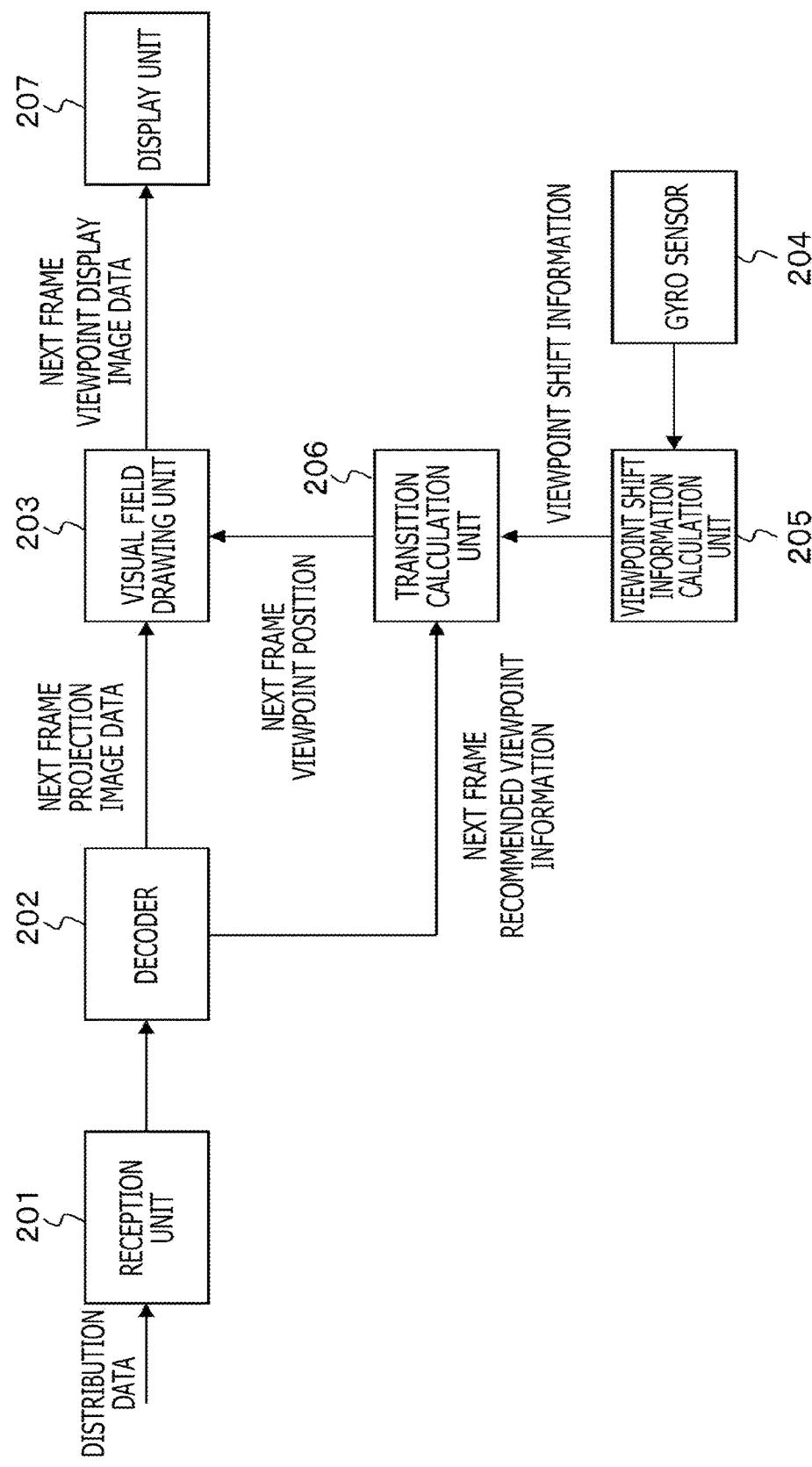
FIG. 3 is a block diagram depicting a configuration example of a display device.

FIG. 3 depicts a configuration example of the display device 200. The display device 200 includes a reception unit 201, a decoder 202, a visual field drawing unit 203, a gyro sensor 204, a viewpoint shift information calculation unit 205, a transition calculation unit 206, and a display unit 207. The transition calculation unit 206 herein constitutes an output range determination unit, while the visual field drawing unit 203 constitutes an output unit.

The reception unit 201 receives a video stream transmitted from the transmission side device as distribution data. The decoder 202 decodes the video stream received by the reception unit 201 to obtain a projection image (image data). In addition, the decoder 202 obtains recommended viewpoint information from the received video stream as information inserted into each frame of the video stream.

The gyro sensor 204 detects a change of a rotation angle of a device housing the gyro sensor 204, i.e., the display device 200 herein. The viewpoint shift information calculation unit 205 calculates viewpoint shift information on the basis of a detection output of the gyro sensor 204. The viewpoint shift information calculation unit 205 constitutes a detection unit that detects a viewpoint position change instruction.

In this configuration, in a case where a user wearing an HMD causes a viewpoint shift by turning the neck, rotating a tablet of the user, or other operations, the viewpoint shift information calculation unit 205 calculates viewpoint shift information indicating this viewpoint shift.

In addition, it may also be considered that the user causes a viewpoint shift by performing a swipe or the like on a touch panel. In this case, the viewpoint shift information calculation unit 205 calculates viewpoint shift information on the basis of information indicating the operation performed for the touch panel.

The transition calculation unit 206 calculates a viewpoint position of a next frame for each frame on the basis of the recommended viewpoint information obtained from the decoder 202 and associated with the next frame, and the viewpoint shift information obtained from the viewpoint shift information calculation unit 205. In a case where a viewpoint shift has been caused by a user operation herein, the transition calculation unit 206 shifts a viewpoint position to reflect a viewpoint shift indicated by the viewpoint shift information, and designates the viewpoint position after the shift as a viewpoint position of the next frame.

On the other hand, in a case where no viewpoint shift is caused by a user operation, the transition calculation unit 206 transits the viewpoint position in a recommended viewpoint direction indicated by the recommended viewpoint information. In this case, a route from a current viewpoint to the recommended viewpoint is interpolated by spherical linear interpolation, and a position advanced by one step is designated as a viewpoint position of the next frame as depicted in FIG. 4. A shift amount of one step is dependent on how many steps are required to return to the recommended viewpoint for interpolation, and therefore becomes a parameter indicating easiness for return. Moreover, in this case, speed control is performed such that an approach speed increases as a difference between the current viewpoint and the recommended viewpoint increases, and such that the approach speed decreases as this difference decreases. In other words, the transition speed is made higher in a case of a larger positional difference than in a case of a smaller positional difference.

FIG. 5(a) depicts an example of a positional relation between a recommended viewpoint and a current viewpoint (display viewpoint) in a rectangular projection image. When no viewpoint shift is caused by a user operation in a state of deviation of the current viewpoint from the recommended viewpoint as a result of a user operation as depicted in the figure, the current viewpoint shifts toward the recommended viewpoint in a direction opposite to the direction of the movement performed by the user as depicted in FIG. 5(b). The example depicted in the figure indicates an example where a current viewpoint of a t–4 frame returns to a recommended viewpoint of a t frame by four frames. The current viewpoint smoothly returns to the recommended viewpoint by lowering the shift speed of the current viewpoint with nearness to the recommended viewpoint.

The visual field drawing unit 203 cuts and renders image data in a viewpoint position range contained in a next frame and calculated by the transition calculation unit 206 from projection image data obtained by the decoder 202 and associated with the next frame, and obtains display image data corresponding to a viewpoint position of the next frame. The display unit 207 displays an image corresponding to display image data of respective frames obtained by the visual field drawing unit 203.

FIG. 6(a) depicts an example of a rectangular projection image. FIG. 6(b) depicts an example of a viewpoint position range in a projection image. In this case, an image corresponding to a viewpoint position is displayed in the display unit 207 as depicted in FIG. 6(c).

An operation of the display device 200 depicted in FIG. 3 will be briefly described. Distribution data transmitted from the transmission side device is received by the reception unit 201 and transmitted to the decoder 202. The decoder 202 decodes a video stream to sequentially obtain projection image data of respective frames. This projection image data is transmitted to the visual field drawing unit 203. In addition, the decoder 202 obtains recommended viewpoint information from a video stream as information inserted for each frame of the video stream. This recommended viewpoint information is transmitted to the transition calculation unit 206.

Moreover, the gyro sensor 204 detects a change of a rotation angle of the display device 200 (e.g., HMD or tablet) housing the gyro sensor 204. A detected output thus obtained is transmitted to the viewpoint shift information calculation unit 205.

The viewpoint shift information calculation unit 205 calculates viewpoint shift information on the basis of the detected output of the gyro sensor 204. In a case where the user wearing the HMD causes a viewpoint shift by turning the neck, rotating the tablet of the user, or other operations herein, the viewpoint shift information calculation unit 205 calculates viewpoint shift information indicating this viewpoint shift. This viewpoint shift information is transmitted to the transition calculation unit 206.

The transition calculation unit 206 calculates a viewpoint position of a next frame for each frame on the basis of recommended viewpoint information obtained from the decoder 202 and associated with the next frame, and viewpoint shift information obtained from the viewpoint shift information calculation unit 205. In a case where a viewpoint shift has been caused by a user operation herein, the transition calculation unit 206 shifts a viewpoint position to reflect a viewpoint shift indicated by the viewpoint shift information, and designates a viewpoint position after the shift as a viewpoint position of the next frame. Moreover, in a case where no viewpoint shift is caused by a user operation, a route from a current viewpoint to a recommended viewpoint is interpolated by spherical linear interpolation such that the viewpoint position transitions in a recommended viewpoint direction indicated by the recommended viewpoint information, and a position advanced by step is designated as a viewpoint position of the next frame.

A viewpoint position of a next frame obtained by the transition calculation unit 206 for each frame is transmitted to the visual field drawing unit 203. The visual field drawing unit 203 cuts and renders image data in a viewpoint position range contained in a next frame and calculated by the transition calculation unit 206 from projection image data obtained by the decoder 202 and associated with the next frame, and obtains display image data corresponding to a viewpoint position of the next frame for each frame.

Display image data of respective frames obtained by the visual field drawing unit 203 is transmitted to the display unit 207. The display unit 207 displays images corresponding to the display image data of the respective frames, i.e., images corresponding to a current viewpoint position.

Figure 7:
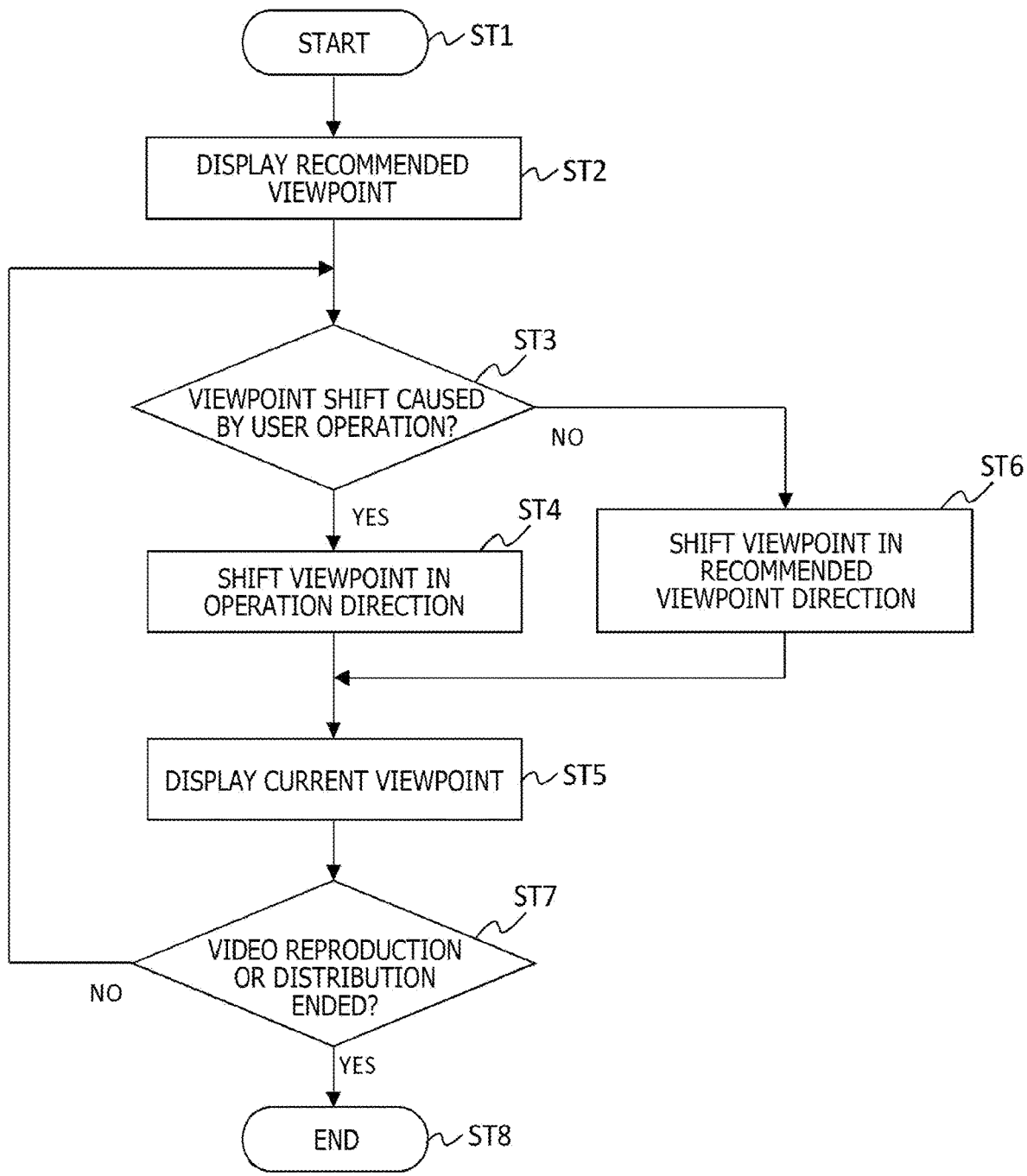
FIG. 7 is a flowchart presenting an example of a display processing procedure performed by the display device.

A flowchart presented in FIG. 7 represents an example of a display processing procedure performed by the display device 200. In step ST1, the display device 200 starts a process in response to a video clip reproduction start operation performed by the user, for example.

Subsequently, the display device 200 in step ST2 displays a range corresponding to a recommended viewpoint (recommended range) as an output range. Thereafter, the display device 200 in step ST3 determines whether or not a viewpoint shift has been caused by a user operation.

In a case where a viewpoint shift has been caused by the user, the display device 200 in step ST4 shifts the viewpoint in an operation direction, and then proceeds to processing in step ST5. In addition, in a case where a shift amount of the viewpoint shift caused by the user operation is small and equivalent to a predetermined value or smaller, a process for determining that no viewpoint shift is caused by a user operation (threshold process) may be performed herein. In this manner, a stable display operation is achievable even in a case where the head wearing the HMD slightly moves, for example. On the other hand, in a case where no viewpoint shift is caused by the user, the display device 200 in step ST6 calculates a route in a recommended viewpoint direction, shifts the viewpoint in the recommended viewpoint direction along the calculated route, and then proceeds to processing in step ST5. In step ST5, the display device 200 displays a range corresponding to a current viewpoint as an output range.

Subsequently, the display device 200 in step ST7 determines whether or not video reproduction or distribution has ended. When it is determined that video reproduction or distribution has not ended yet, the display device 200 returns to processing in step ST3 and reflects a process for a next frame. On the other hand, when it is determined that video reproduction or distribution has ended, a series of processes end in step ST8.

Note that the series of processes performed by the display device 200 as described above may be executed by hardware, or may be executed by software. In a case where the series of processes are executed by software, a program constituting the software is installed in a computer. Examples of the computer herein include a computer incorporated in dedicated hardware, and a computer capable of executing various functions under various programs installed in the computer, such as a general-purpose personal computer.

Figure 8:
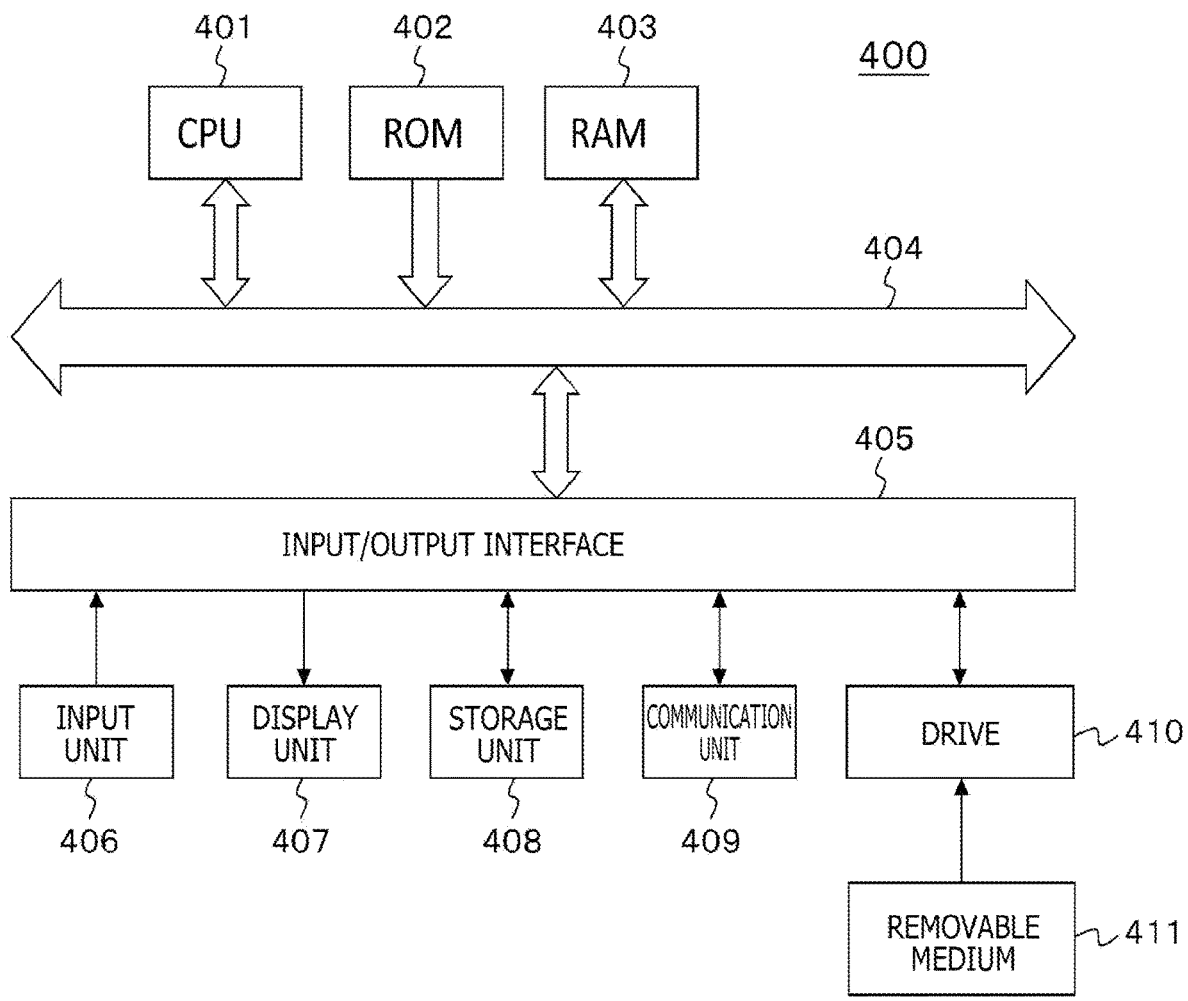
FIG. 8 is a block diagram depicting a configuration example of hardware of a computer.

FIG. 8 is a block diagram depicting a hardware configuration example of a computer 400 which executes the series of processes described above under a program.

The computer 400 includes a CPU (Central Processing Unit) 401, a ROM (Read Only Memory) 402, and a RAM (Random Access Memory) 403 connected to each other via a bus 404.

An input/output interface 405 is further connected to the bus 404. An input unit 406, an output unit 407, a recording unit 408, a communication unit 409, and a drive 410 are connected to the input/output interface 405.

The input unit 406 includes an input switch, buttons, a microphone, an imaging element, and others. The output unit 407 includes a display, a speaker, and others. The recording unit 408 includes a hard disk, a non-volatile memory, and others. The communication unit 409 includes a network interface and others. The drive 410 drives a removable medium 411 such as a magnetic disk, an optical disk, a magneto-optical disk, and a semiconductor memory.

According to the computer 400 configured as described above, for example, the CPU 401 loads a program stored in the recording unit 408 into the RAM 403 via the input/output interface 405 and the bus 404, and executes the loaded program to perform the series of processes described above.

For example, the program executed by the computer 400 (CPU 401) is allowed to be recorded in the removable medium 411 as a package medium or the like, and provided in this form. In addition, the program is allowed to be provided via a wired or wireless transfer medium such as a local area network, the Internet, and digital satellite broadcasting.

In the computer, the program is allowed to be installed into the recording unit 408 via the input/output interface 405 by attaching the removable medium 411 to the drive 410. Moreover, the program is allowed to be received by the communication unit 409 via a wired or wireless transfer medium, and installed in the recording unit 408. Furthermore, the program is allowed to be installed in the ROM 402 or the recording unit 408 beforehand.

Note that the program executed by the computer may be a program under which processes are performed in time series in the order described in the present description, or may be a program under which processes are performed in parallel or at necessary timing such as an occasion of a call.

As described above, the display device 200 of the image distribution system 10 depicted in FIG. 1 is capable of changing an output range according to a viewpoint shift caused by a user operation after designating a recommended range (a range corresponding to a recommended viewpoint) as the output range, and transits the output range in a direction of the recommended range in a case where the output range deviates from the recommended range in a state of no viewpoint shift caused by a user operation. Accordingly, combined use of a recommended viewpoint and a free viewpoint is achievable without display of a position of the recommended viewpoint using a frame or the like.

2. Application

The technology according to the present disclosure is applicable to various products. For example, the technology according to the present disclosure is applicable to an operation room system.

Figure 9:
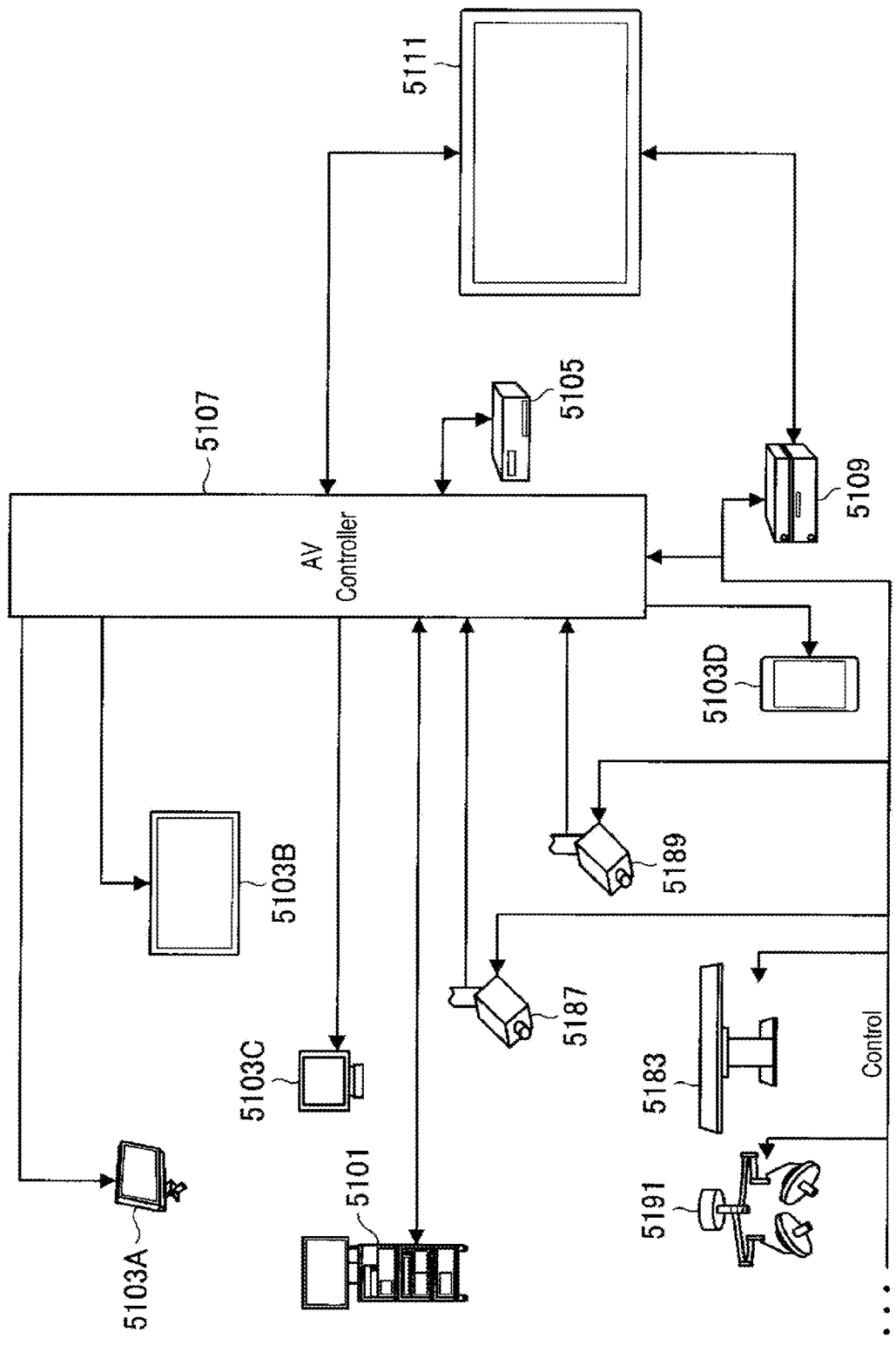
FIG. 9 is a view schematically depicting a general configuration of an operating room system.

FIG. 9 is a view schematically depicting a general configuration of an operating room system 5100 to which the technology according to an embodiment of the present disclosure can be applied. Referring to FIG. 9, the operating room system 5100 is configured such that a group of apparatus installed in an operating room are connected for cooperation with each other through an audiovisual (AV) controller 5107 and an operating room controlling apparatus 5109.

In the operating room, various apparatus may be installed. In FIG. 9, as an example, various apparatus group 5101 for endoscopic surgery, a ceiling camera 5187, a surgery field camera 5189, a plurality of display apparatus 5103A to 5103D, a recorder 5105, a patient bed 5183 and an illumination 5191 are depicted. The ceiling camera 5187 is provided on the ceiling of an operating room and images the hands of a surgeon. The surgery field camera 5189 is provided on the ceiling of the operating room and images a state of the entire operating room.

Among the apparatus mentioned, the apparatus group 5101 belongs to an endoscopic surgery system 5113 hereinafter described and include an endoscope, a display apparatus which displays an image picked up by the endoscope and so forth. Various apparatus belonging to the endoscopic surgery system 5113 are referred to also as medical equipment. Meanwhile, the display apparatus 5103A to 5103D, the recorder 5105, the patient bed 5183 and the illumination 5191 are apparatus which are equipped, for example, in the operating room separately from the endoscopic surgery system 5113. The apparatus which do not belong to the endoscopic surgery system 5113 are referred to also as non-medical equipment. The audiovisual controller 5107 and/or the operating room controlling apparatus 5109 cooperatively control operation of the medical equipment and the non-medical equipment with each other.

The audiovisual controller 5107 integrally controls processes of the medical equipment and the non-medical equipment relating to image display. Specifically, each of the apparatus group 5101, the ceiling camera 5187 and the surgery field camera 5189 from among the apparatus provided in the operating room system 5100 may be an apparatus having a function of sending information to be displayed during surgery (such information is hereinafter referred to as display information, and the apparatus mentioned is hereinafter referred to as apparatus of a sending source). Meanwhile, each of the display apparatus 5103A to 5103D may be an apparatus to which display information is outputted (the apparatus is hereinafter referred to also as apparatus of an output destination). Further, the recorder 5105 may be an apparatus which serves as both of an apparatus of a sending source and an apparatus of an output destination. The audiovisual controller 5107 has a function of controlling operation of an apparatus of a sending source and an apparatus of an output destination to acquire display information from the apparatus of a sending source and transmit the display information to the apparatus of an output destination so as to be displayed or recorded. It is to be noted that the display information includes various images picked up during surgery, various kinds of information relating to the surgery (for example, physical information of a patient, inspection results in the past or information regarding a surgical procedure) and so forth.

Specifically, to the audiovisual controller 5107, information relating to an image of a surgical region in a body cavity of a patient imaged by the endoscope may be transmitted as the display information from the apparatus group 5101. Further, from the ceiling camera 5187, information relating to an image of the hands of the surgeon picked up by the ceiling camera 5187 may be transmitted as display information. Further, from the surgery field camera 5189, information relating to an image picked up by the surgery field camera 5189 and illustrating a state of the entire operating room may be transmitted as display information. It is to be noted that, if a different apparatus having an image pickup function exists in the operating room system 5100, then the audiovisual controller 5107 may acquire information relating to an image picked up by the different apparatus as display information also from the different apparatus.

Alternatively, for example, in the recorder 5105, information relating to such images as mentioned above picked up in the past is recorded by the audiovisual controller 5107. The audiovisual controller 5107 can acquire, as display information, information relating to the images picked up in the past from the recorder 5105. It is to be noted that also various pieces of information relating to surgery may be recorded in advance in the recorder 5105.

The audiovisual controller 5107 controls at least one of the display apparatus 5103A to 5103D, which are apparatus of an output destination, to display acquired display information (namely, images picked up during surgery or various pieces of information relating to the surgery). In the example depicted, the display apparatus 5103A is a display apparatus installed so as to be suspended from the ceiling of the operating room; the display apparatus 5103B is a display apparatus installed on a wall face of the operating room; the display apparatus 5103C is a display apparatus installed on a desk in the operating room; and the display apparatus 5103D is a mobile apparatus (for example, a tablet personal computer (PC)) having a display function.

Further, though not depicted in FIG. 9, the operating room system 5100 may include an apparatus outside the operating room. The apparatus outside the operating room may be, for example, a server connected to a network constructed inside and outside the hospital, a PC used by medical staff, a projector installed in a meeting room of the hospital or the like. Where such an external apparatus is located outside the hospital, also it is possible for the audiovisual controller 5107 to cause display information to be displayed on a display apparatus of a different hospital through a teleconferencing system or the like to perform telemedicine.

The operating room controlling apparatus 5109 integrally controls processes other than processes relating to image display on the non-medical equipment. For example, the operating room controlling apparatus 5109 controls driving of the patient bed 5183, the ceiling camera 5187, the surgery field camera 5189 and the illumination 5191.

In the operating room system 5100, a centralized operation panel 5111 is provided such that it is possible to issue an instruction regarding image display to the audiovisual controller 5107 or issue an instruction regarding operation of the non-medical equipment to the operating room controlling apparatus 5109 through the centralized operation panel 5111. The centralized operation panel 5111 is configured by providing a touch panel on a display face of a display apparatus.

Figure 10:
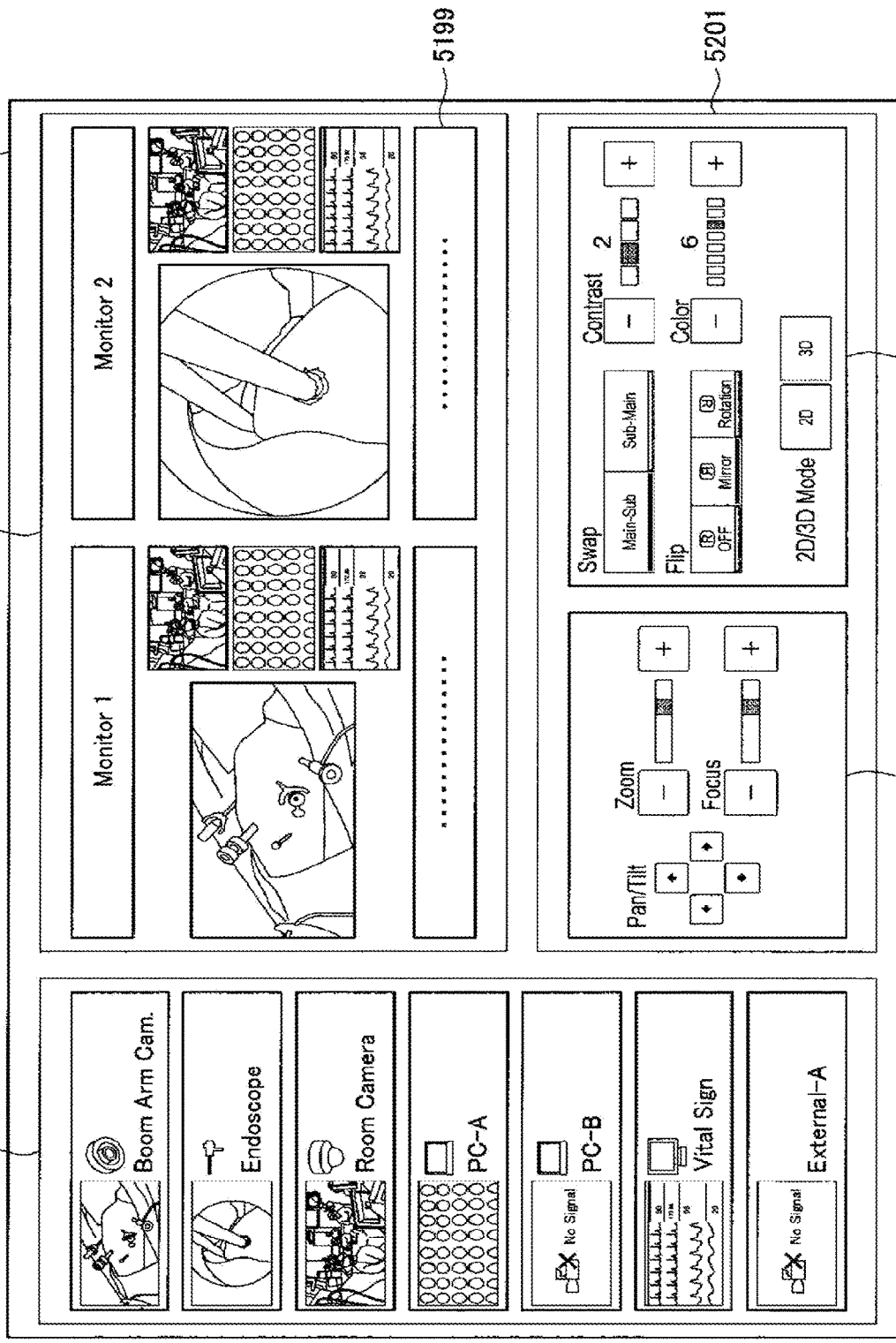
FIG. 10 is a view depicting an example of display of an operation screen image of a centralized operation panel.

FIG. 10 is a view depicting an example of display of an operation screen image on the centralized operation panel 5111. In FIG. 10, as an example, an operation screen image is depicted which corresponds to a case in which two display apparatus are provided as apparatus of an output destination in the operating room system 5100. Referring to FIG. 10, the operation screen image 5193 includes a sending source selection region 5195, a preview region 5197 and a control region 5201.

In the sending source selection region 5195, the sending source apparatus provided in the operating room system 5100 and thumbnail screen images representative of display information the sending source apparatus have are displayed in an associated manner with each other. A user can select display information to be displayed on the display apparatus from any of the sending source apparatus displayed in the sending source selection region 5195.

In the preview region 5197, a preview of screen images displayed on two display apparatus (Monitor 1 and Monitor 2) which are apparatus of an output destination is displayed. In the example depicted, four images are displayed by picture in picture (PinP) display in regard to one display apparatus. The four images correspond to display information sent from the sending source apparatus selected in the sending source selection region 5195. One of the four images is displayed in a comparatively large size as a main image while the remaining three images are displayed in a comparatively small size as sub images. The user can exchange between the main image and the sub images by suitably selecting one of the images from among the four images displayed in the region. Further, a status displaying region 5199 is provided below the region in which the four images are displayed, and a status relating to surgery (for example, elapsed time of the surgery, physical information of the patient and so forth) may be displayed suitably in the status displaying region 5199.

A sending source operation region 5203 and an output destination operation region 5205 are provided in the control region 5201. In the sending source operation region 5203, a graphical user interface (GUI) part for performing an operation for an apparatus of a sending source is displayed. In the output destination operation region 5205, a GUI part for performing an operation for an apparatus of an output destination is displayed. In the example depicted, GUI parts for performing various operations for a camera (panning, tilting and zooming) in an apparatus of a sending source having an image pickup function are provided in the sending source operation region 5203. The user can control operation of the camera of an apparatus of a sending source by suitably selecting any of the GUI parts. It is to be noted that, though not depicted, where the apparatus of a sending source selected in the sending source selection region 5195 is a recorder (namely, where an image recorded in the recorder in the past is displayed in the preview region 5197), GUI parts for performing such operations as reproduction of the image, stopping of reproduction, rewinding, fast-feeding and so forth may be provided in the sending source operation region 5203.

Further, in the output destination operation region 5205, GUI parts for performing various operations for display on a display apparatus which is an apparatus of an output destination (swap, flip, color adjustment, contrast adjustment and switching between two dimensional (2D) display and three dimensional (3D) display) are provided. The user can operate the display of the display apparatus by suitably selecting any of the GUI parts.

It is to be noted that the operation screen image to be displayed on the centralized operation panel 5111 is not limited to the depicted example, and the user may be able to perform operation inputting to each apparatus which can be controlled by the audiovisual controller 5107 and the operating room controlling apparatus 5109 provided in the operating room system 5100 through the centralized operation panel 5111.

Figure 11:
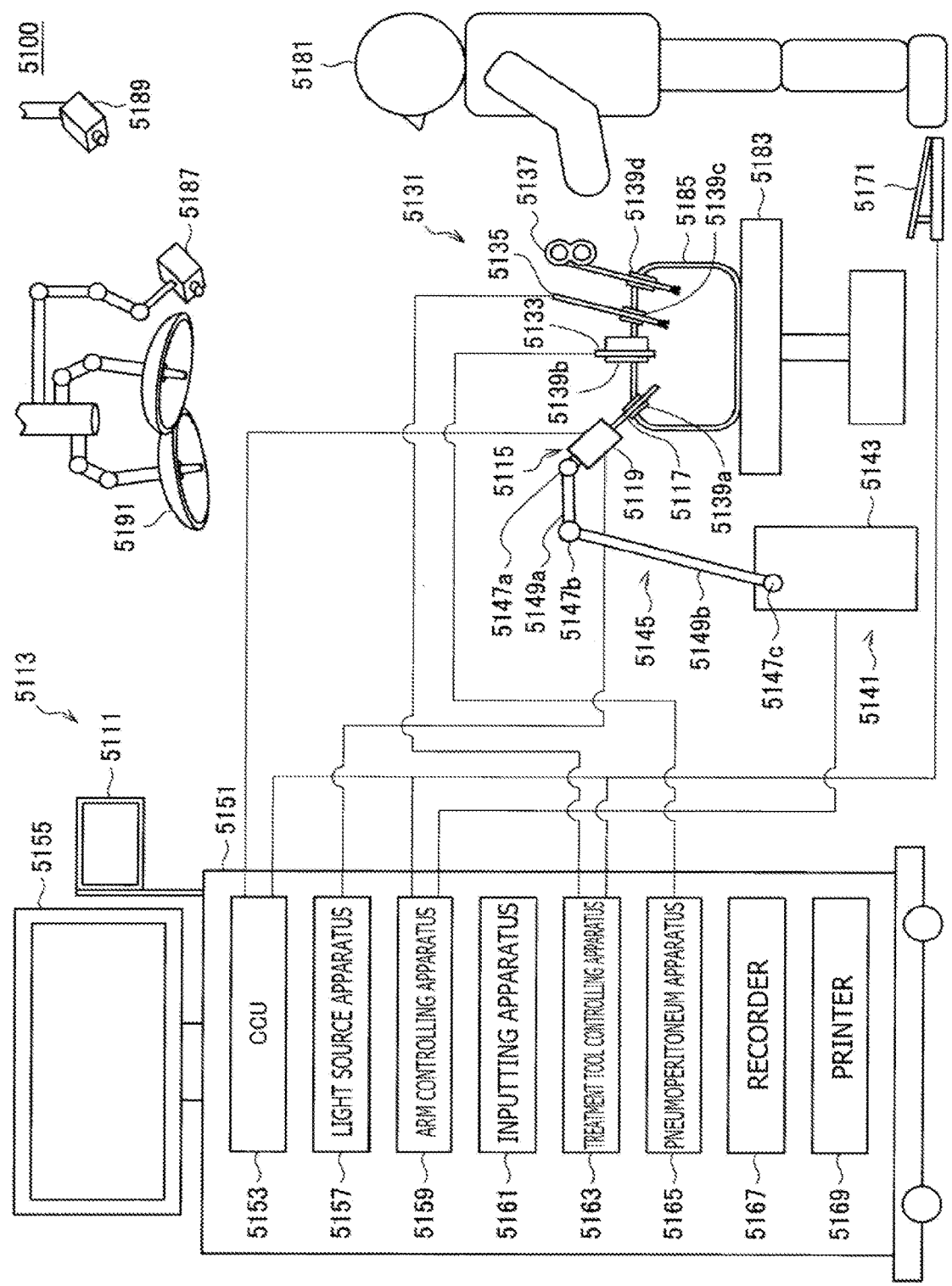
FIG. 11 is a view illustrating an example of a state of surgery to which the operating room system is applied.

FIG. 11 is a view illustrating an example of a state of surgery to which the operating room system described above is applied. The ceiling camera 5187 and the surgery field camera 5189 are provided on the ceiling of the operating room such that it can image the hands of a surgeon (medical doctor) 5181 who performs treatment for an affected area of a patient 5185 on the patient bed 5183 and the entire operating room. The ceiling camera 5187 and the surgery field camera 5189 may include a magnification adjustment function, a focal distance adjustment function, an imaging direction adjustment function and so forth. The illumination 5191 is provided on the ceiling of the operating room and irradiates at least upon the hands of the surgeon 5181. The illumination 5191 may be configured such that the irradiation light amount, the wavelength (color) of the irradiation light, the irradiation direction of the light and so forth can be adjusted suitably.

The endoscopic surgery system 5113, the patient bed 5183, the ceiling camera 5187, the surgery field camera 5189 and the illumination 5191 are connected for cooperation with each other through the audiovisual controller 5107 and the operating room controlling apparatus 5109 (not depicted in FIG. 11) as depicted in FIG. 9. The centralized operation panel 5111 is provided in the operating room, and the user can suitably operate the apparatus existing in the operating room through the centralized operation panel 5111 as described hereinabove.

In the following, a configuration of the endoscopic surgery system 5113 is described in detail. As depicted, the endoscopic surgery system 5113 includes an endoscope 5115, other surgical tools 5131, a supporting arm apparatus 5141 which supports the endoscope 5115 thereon, and a cart 5151 on which various apparatus for endoscopic surgery are mounted.

In endoscopic surgery, in place of incision of the abdominal wall to perform laparotomy, a plurality of tubular aperture devices called trocars 5139*a* to 5139*d* are used to puncture the abdominal wall. Then, a lens barrel 5117 of the endoscope 5115 and the other surgical tools 5131 are inserted into body cavity of the patient 5185 through the trocars 5139*a* to 5139*d*. In the example depicted, as the other surgical tools 5131, a pneumoperitoneum tube 5133, an energy device 5135 and forceps 5137 are inserted into body cavity of the patient 5185. Further, the energy device 5135 is a treatment tool for performing incision and peeling of a tissue, sealing of a blood vessel or the like by high frequency current or ultrasonic vibration. However, the surgical tools 5131 depicted are mere examples at all, and as the surgical tools 5131, various surgical tools which are generally used in endoscopic surgery such as, for example, tweezers or a retractor may be used.

An image of a surgical region in a body cavity of the patient 5185 picked up by the endoscope 5115 is displayed on a display apparatus 5155. The surgeon 5181 would use the energy device 5135 or the forceps 5137 while watching the image of the surgical region displayed on the display apparatus 5155 on the real time basis to perform such treatment as, for example, resection of an affected area. It is to be noted that, though not depicted, the pneumoperitoneum tube 5133, the energy device 5135, and the forceps 5137 are supported by the surgeon 5181, an assistant or the like during surgery.

(Supporting Arm Apparatus)

The supporting arm apparatus 5141 includes an arm unit 5145 extending from a base unit 5143. In the example depicted, the arm unit 5145 includes joint portions 5147a, 5147b and 5147c and links 5149a and 5149b and is driven under the control of an arm controlling apparatus 5159. The endoscope 5115 is supported by the arm unit 5145 such that the position and the posture of the endoscope 5115 are controlled. Consequently, stable fixation in position of the endoscope 5115 can be implemented.

(Endoscope)

The endoscope 5115 includes the lens barrel 5117 which has a region of a predetermined length from a distal end thereof to be inserted into a body cavity of the patient 5185, and a camera head 5119 connected to a proximal end of the lens barrel 5117. In the example depicted, the endoscope 5115 is depicted as a rigid endoscope having the lens barrel 5117 of the hard type. However, the endoscope 5115 may otherwise be configured as a flexible endoscope having the lens barrel 5117 of the flexible type.

The lens barrel 5117 has, at a distal end thereof, an opening in which an objective lens is fitted. A light source apparatus 5157 is connected to the endoscope 5115 such that light generated by the light source apparatus 5157 is introduced to a distal end of the lens barrel 5117 by a light guide extending in the inside of the lens barrel 5117 and is applied toward an observation target in a body cavity of the patient 5185 through the objective lens. It is to be noted that the endoscope 5115 may be a forward-viewing endoscope or may be an oblique-viewing endoscope or a side-viewing endoscope.

An optical system and an image pickup element are provided in the inside of the camera head 5119 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5153. It is to be noted that the camera head 5119 has a function incorporated therein for suitably driving the optical system of the camera head 5119 to adjust the magnification and the focal distance.

It is to be noted that, in order to establish compatibility with, for example, a stereoscopic vision (3D display), a plurality of image pickup elements may be provided on the camera head 5119. In this case, a plurality of relay optical systems are provided in the inside of the lens barrel 5117 in order to guide observation light to the plurality of respective image pickup elements.

(Various Apparatus Incorporated in Cart)

The CCU 5153 includes a central processing unit (CPU), a graphics processing unit (GPU) or the like and integrally controls operation of the endoscope 5115 and the display apparatus 5155. Specifically, the CCU 5153 performs, for an image signal received from the camera head 5119, various image processes for displaying an image based on the image signal such as, for example, a development process (demosaic process). The CCU 5153 provides the image signal for which the image processes have been performed to the display apparatus 5155. Further, the audiovisual controller 5107 depicted in FIG. 9 is connected to the CCU 5153. The CCU 5153 provides the image signal for which the image processes have been performed also to the audiovisual controller 5107. Further, the CCU 5153 transmits a control signal to the camera head 5119 to control driving of the camera head 5119. The control signal may include information relating to an image pickup condition such as a magnification or a focal distance. The information relating to an image pickup condition may be inputted through the inputting apparatus 5161 or may be inputted through the centralized operation panel 5111 described hereinabove.

The display apparatus 5155 displays an image based on an image signal for which the image processes have been performed by the CCU 5153 under the control of the CCU 5153. If the endoscope 5115 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5155. Where the apparatus is ready for imaging of a high resolution such as 4K or 8K, if the display apparatus used as the display apparatus 5155 has a size of equal to or not less than 55 inches, then a more immersive experience can be obtained. Further, a plurality of display apparatus 5155 having different resolutions and/or different sizes may be provided in accordance with purposes.

The light source apparatus 5157 includes a light source such as, for example, a light emitting diode (LED) and supplies irradiation light for imaging of a surgical region to the endoscope 5115.

The arm controlling apparatus 5159 includes a processor such as, for example, a CPU and operates in accordance with a predetermined program to control driving of the arm unit 5145 of the supporting arm apparatus 5141 in accordance with a predetermined controlling method.

An inputting apparatus 5161 is an input interface for the endoscopic surgery system 5113. A user can perform inputting of various kinds of information or instruction inputting to the endoscopic surgery system 5113 through the inputting apparatus 5161. For example, the user would input various kinds of information relating to surgery such as physical information of a patient, information regarding a surgical procedure of the surgery and so forth through the inputting apparatus 5161. Further, the user would input, for example, an instruction to drive the arm unit 5145, an instruction to change an image pickup condition (type of irradiation light, magnification, focal distance or the like) by the endoscope 5115, an instruction to drive the energy device 5135 or a like through the inputting apparatus 5161.

The type of the inputting apparatus 5161 is not limited and may be that of any one of various known inputting apparatus. As the inputting apparatus 5161, for example, a mouse, a keyboard, a touch panel, a switch, a foot switch 5171 and/or a lever or the like may be applied. Where a touch panel is used as the inputting apparatus 5161, it may be provided on the display face of the display apparatus 5155.

The inputting apparatus 5161 is otherwise a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5161 includes a camera which can detect a motion of a user, and various kinds of inputting are performed in response to a gesture or a line of sight of a user detected from a video picked up by the camera. Further, the inputting apparatus 5161 includes a microphone which can collect the voice of a user, and various kinds of inputting are performed by voice through the microphone. By configuring the inputting apparatus 5161 such that various kinds of information can be inputted in a contactless fashion in this manner, especially a user who belongs to a clean area (for example, the surgeon 5181) can operate an apparatus belonging to an unclean area in a contactless fashion. Further, since the user can operate an apparatus without releasing a possessed surgical tool from its hand, the convenience to the user is improved.

A treatment tool controlling apparatus 5163 controls driving of the energy device 5135 for cautery or incision of a tissue, sealing of a blood vessel or the like. A pneumoperitoneum apparatus 5165 feeds gas into a body cavity of the patient 5185 through the pneumoperitoneum tube 5133 to inflate the body cavity in order to secure the field of view of the endoscope 5115 and secure the working space for the surgeon. A recorder 5167 is an apparatus capable of recording various kinds of information relating to surgery. A printer 5169 is an apparatus capable of printing various kinds of information relating to surgery in various forms such as a text, an image or a graph.

In the following, especially a characteristic configuration of the endoscopic surgery system 5113 is described in more detail.

(Supporting Arm Apparatus)

The supporting arm apparatus 5141 includes the base unit 5143 serving as a base, and the arm unit 5145 extending from the base unit 5143. In the example depicted, the arm unit 5145 includes the plurality of joint portions 5147*a*, 5147*b* and 5147*c* and the plurality of links 5149*a* and 5149*b* connected to each other by the joint portion 5147*b*. In FIG. 11, for simplified illustration, the configuration of the arm unit 5145 is depicted in a simplified form. Actually, the shape, number and arrangement of the joint portions 5147*a* to 5147*c* and the links 5149*a* and 5149*b* and the direction and so forth of axes of rotation of the joint portions 5147*a* to 5147*c* can be set suitably such that the arm unit 5145 has a desired degree of freedom. For example, the arm unit 5145 may preferably be included such that it has a degree of freedom equal to or not less than 6 degrees of freedom. This makes it possible to move the endoscope 5115 freely within the movable range of the arm unit 5145. Consequently, it becomes possible to insert the lens barrel 5117 of the endoscope 5115 from a desired direction into a body cavity of the patient 5185.

An actuator is provided in the joint portions 5147*a* to 5147*c*, and the joint portions 5147*a* to 5147*c* include such that they are rotatable around predetermined axes of rotation thereof by driving of the actuator. The driving of the actuator is controlled by the arm controlling apparatus 5159 to control the rotational angle of each of the joint portions 5147*a* to 5147*c* thereby to control driving of the arm unit 5145. Consequently, control of the position and the posture of the endoscope 5115 can be implemented. Thereupon, the arm controlling apparatus 5159 can control driving of the arm unit 5145 by various known controlling methods such as force control or position control.

For example, if the surgeon 5181 suitably performs operation inputting through the inputting apparatus 5161 (including the foot switch 5171), then driving of the arm unit 5145 may be controlled suitably by the arm controlling apparatus 5159 in response to the operation input to control the position and the posture of the endoscope 5115. After the endoscope 5115 at the distal end of the arm unit 5145 is moved from an arbitrary position to a different arbitrary position by the control just described, the endoscope 5115 can be supported fixedly at the position after the movement. It is to be noted that the arm unit 5145 may be operated in a master-slave fashion. In this case, the arm unit 5145 may be remotely controlled by the user through the inputting apparatus 5161 which is placed at a place remote from the operating room.

Further, where force control is applied, the arm controlling apparatus 5159 may perform power-assisted control to drive the actuators of the joint portions 5147*a* to 5147*c* such that the arm unit 5145 may receive external force by the user and move smoothly following the external force. This makes it possible to move the arm unit 5145 with comparatively weak force when the user directly touches with and moves the arm unit 5145. Accordingly, it becomes possible for the user to move the endoscope 5115 more intuitively by a simpler and easier operation, and the convenience to the user can be improved.

Here, generally in endoscopic surgery, the endoscope 5115 is supported by a medical doctor called scopist. In contrast, where the supporting arm apparatus 5141 is used, the position of the endoscope 5115 can be fixed with a higher degree of certainty without hands, and therefore, an image of a surgical region can be obtained stably and surgery can be performed smoothly.

It is to be noted that the arm controlling apparatus 5159 may not necessarily be provided on the cart 5151. Further, the arm controlling apparatus 5159 may not necessarily be a single apparatus. For example, the arm controlling apparatus 5159 may be provided in each of the joint portions 5147*a* to 5147*c* of the arm unit 5145 of the supporting arm apparatus 5141 such that the plurality of arm controlling apparatus 5159 cooperate with each other to implement driving control of the arm unit 5145.

(Light Source Apparatus)

The light source apparatus 5157 supplies irradiation light upon imaging of a surgical region to the endoscope 5115. The light source apparatus 5157 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5157. Further, in this case, if laser beams from the RGB laser light sources are applied time-divisionally on an observation target and driving of the image pickup elements of the camera head 5119 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5157 may be controlled such that the intensity of light to be outputted is changed for each predetermined time. By controlling driving of the image pickup element of the camera head 5119 in synchronism with the timing of the change of the intensity of light to acquire images time-divisionally and synthesizing the images, an image of a high dynamic range free from underexposed blocked up shadows and overexposed highlights can be created.

Further, the light source apparatus 5157 may be configured to supply light of a predetermined wavelength band ready for special light observation. In special light observation, for example, by utilizing the wavelength dependency of absorption of light of a body tissue, narrow band light observation (narrow band imaging) of imaging a predetermined tissue such as a blood vessel of a superficial portion of the mucous membrane or the like in a high contrast is performed by applying light of a narrower wavelength band in comparison with irradiation light upon ordinary observation (namely, white light). Alternatively, in special light observation, fluorescent observation for obtaining an image from fluorescent light generated by irradiation of excitation light may also be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5157 can be configured to supply such narrow-band light and/or excitation light suitable for special light observation as described above.

(Camera Head and CCU)

Figure 12:
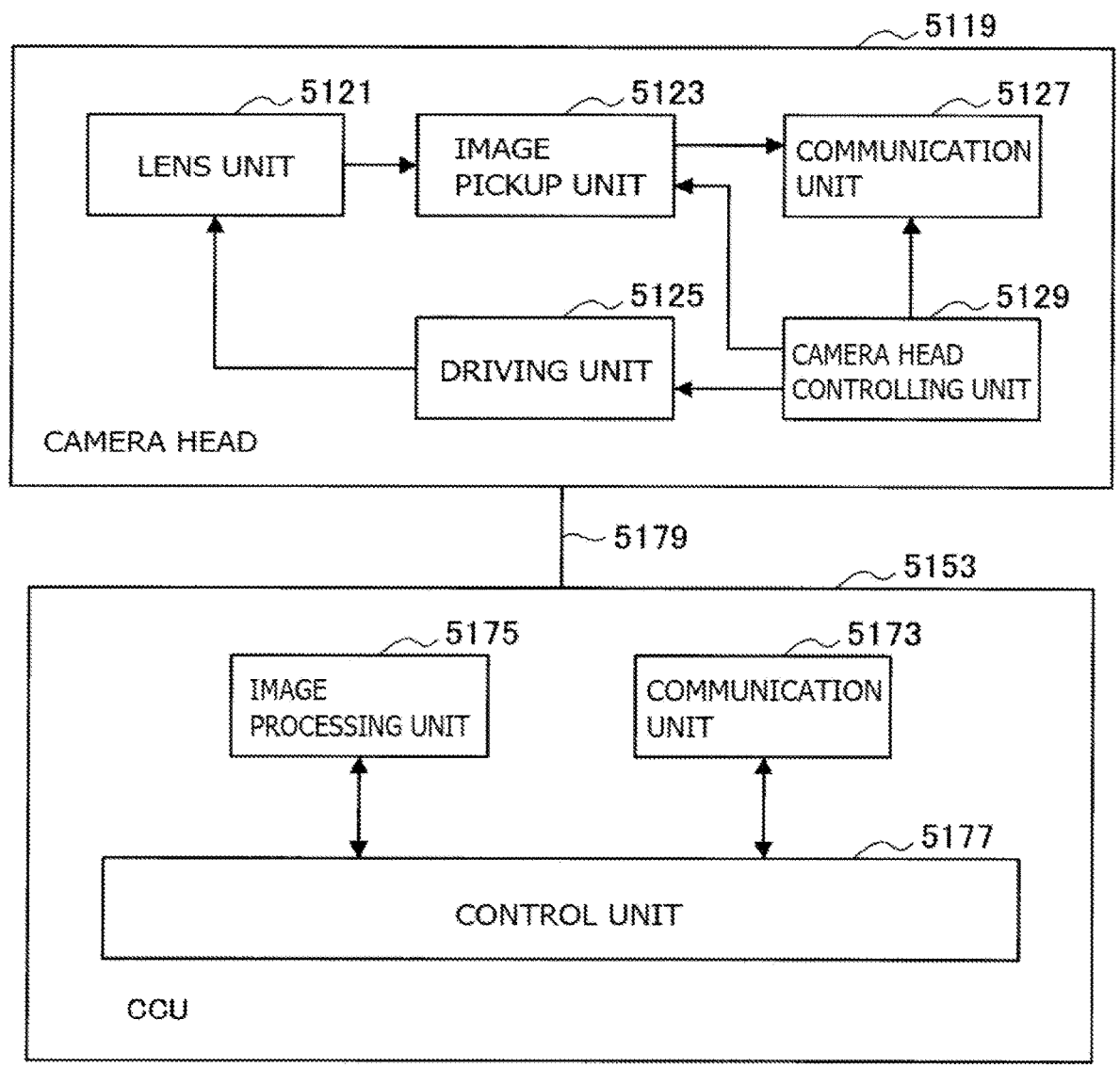
FIG. 12 is a block diagram depicting an example of a functional configuration of a camera head and a camera control unit (CCU) depicted in FIG. 11.

Functions of the camera head 5119 of the endoscope 5115 and the CCU 5153 are described in more detail with reference to FIG. 12. FIG. 12 is a block diagram depicting an example of a functional configuration of the camera head 5119 and the CCU 5153 depicted in FIG. 11.

Referring to FIG. 12, the camera head 5119 has, as functions thereof, a lens unit 5121, an image pickup unit 5123, a driving unit 5125, a communication unit 5127 and a camera head controlling unit 5129. Further, the CCU 5153 has, as functions thereof, a communication unit 5173, an image processing unit 5175 and a control unit 5177. The camera head 5119 and the CCU 5153 are connected to be bidirectionally communicable to each other by a transmission cable 5179.

First, a functional configuration of the camera head 5119 is described. The lens unit 5121 is an optical system provided at a connecting location of the camera head 5119 to the lens barrel 5117. Observation light taken in from a distal end of the lens barrel 5117 is introduced into the camera head 5119 and enters the lens unit 5121. The lens unit 5121 includes a combination of a plurality of lenses including a zoom lens and a focusing lens. The lens unit 5121 has optical properties adjusted such that the observation light is condensed on a light receiving face of the image pickup element of the image pickup unit 5123. Further, the zoom lens and the focusing lens include such that the positions thereof on their optical axis are movable for adjustment of the magnification and the focal point of a picked up image.

The image pickup unit 5123 includes an image pickup element and disposed at a succeeding stage to the lens unit 5121. Observation light having passed through the lens unit 5121 is condensed on the light receiving face of the image pickup element, and an image signal corresponding to the observation image is generated by photoelectric conversion. The image signal generated by the image pickup unit 5123 is provided to the communication unit 5127.

As the image pickup element which is included by the image pickup unit 5123, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5181 can comprehend a state of the surgical region in enhanced details and can proceed with the surgery more smoothly.

Further, the image pickup element which is included by the image pickup unit 5123 is configured such that it has a pair of image pickup elements for acquiring image signals for the right eye and the left eye compatible with 3D display. Where 3D display is applied, the surgeon 5181 can comprehend the depth of a living body tissue in the surgical region with a higher degree of accuracy. It is to be noted that, if the image pickup unit 5123 is configured as that of the multi-plate type, then a plurality of systems of lens units 5121 are provided corresponding to the individual image pickup elements of the image pickup unit 5123.

The image pickup unit 5123 may not necessarily be provided on the camera head 5119. For example, the image pickup unit 5123 may be provided just behind the objective lens in the inside of the lens barrel 5117.

The driving unit 5125 includes an actuator and moves the zoom lens and the focusing lens of the lens unit 5121 by a predetermined distance along the optical axis under the control of the camera head controlling unit 5129. Consequently, the magnification and the focal point of a picked up image by the image pickup unit 5123 can be adjusted suitably.

The communication unit 5127 includes a communication apparatus for transmitting and receiving various kinds of information to and from the CCU 5153. The communication unit 5127 transmits an image signal acquired from the image pickup unit 5123 as RAW data to the CCU 5153 through the transmission cable 5179. Thereupon, in order to display a picked up image of a surgical region in low latency, preferably the image signal is transmitted by optical communication. This is because, since, upon surgery, the surgeon 5181 performs surgery while observing the state of an affected area through a picked up image, in order to achieve surgery with a higher degree of safety and certainty, it is demanded for a moving image of the surgical region to be displayed on the real time basis as far as possible. Where optical communication is applied, a photoelectric conversion module for converting an electric signal into an optical signal is provided in the communication unit 5127. After the image signal is converted into an optical signal by the photoelectric conversion module, it is transmitted to the CCU 5153 through the transmission cable 5179.

Further, the communication unit 5127 receives a control signal for controlling driving of the camera head 5119 from the CCU 5153. The control signal includes information relating to image pickup conditions such as, for example, information that a frame rate of a picked up image is designated, information that an exposure value upon image picking up is designated and/or information that a magnification and a focal point of a picked up image are designated. The communication unit 5127 provides the received control signal to the camera head controlling unit 5129. It is to be noted that also the control signal from the CCU 5153 may be transmitted by optical communication. In this case, a photoelectric conversion module for converting an optical signal into an electric signal is provided in the communication unit 5127. After the control signal is converted into an electric signal by the photoelectric conversion module, it is provided to the camera head controlling unit 5129.

It is to be noted that the image pickup conditions such as the frame rate, exposure value, magnification or focal point are set automatically by the control unit 5177 of the CCU 5153 on the basis of an acquired image signal. In other words, an auto exposure (AE) function, an auto focus (AF) function and an auto white balance (AWB) function are incorporated in the endoscope 5115.

The camera head controlling unit 5129 controls driving of the camera head 5119 on the basis of a control signal from the CCU 5153 received through the communication unit 5127. For example, the camera head controlling unit 5129 controls driving of the image pickup element of the image pickup unit 5123 on the basis of information that a frame rate of a picked up image is designated and/or information that an exposure value upon image picking up is designated. Further, for example, the camera head controlling unit 5129 controls the driving unit 5125 to suitably move the zoom lens and the focus lens of the lens unit 5121 on the basis of information that a magnification and a focal point of a picked up image are designated. The camera head controlling unit 5129 may include a function for storing information for identifying of the lens barrel 5117 and/or the camera head 5119.

It is to be noted that, by disposing the components such as the lens unit 5121 and the image pickup unit 5123 in a sealed structure having high airtightness and high waterproof, the camera head 5119 can be provided with resistance to an autoclave sterilization process.

Now, a functional configuration of the CCU 5153 is described. The communication unit 5173 includes a communication apparatus for transmitting and receiving various kinds of information to and from the camera head 5119. The communication unit 5173 receives an image signal transmitted thereto from the camera head 5119 through the transmission cable 5179. Thereupon, the image signal may be transmitted preferably by optical communication as described above. In this case, for the compatibility with optical communication, the communication unit 5173 includes a photoelectric conversion module for converting an optical signal into an electric signal. The communication unit 5173 provides the image signal after conversion into an electric signal to the image processing unit 5175.

Further, the communication unit 5173 transmits, to the camera head 5119, a control signal for controlling driving of the camera head 5119. Also the control signal may be transmitted by optical communication.

The image processing unit 5175 performs various image processes for an image signal in the form of RAW data transmitted thereto from the camera head 5119. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5175 performs a detection process for an image signal for performing AE, AF and AWB.

The image processing unit 5175 includes a processor such as a CPU or a GPU, and when the processor operates in accordance with a predetermined program, the image processes and the detection process described above can be performed. It is to be noted that, where the image processing unit 5175 includes a plurality of GPUs, the image processing unit 5175 suitably divides information relating to an image signal such that image processes are performed in parallel by the plurality of GPUs.

The control unit 5177 performs various kinds of control relating to image picking up of a surgical region by the endoscope 5115 and display of the picked up image. For example, the control unit 5177 generates a control signal for controlling driving of the camera head 5119. Thereupon, if image pickup conditions are inputted by the user, then the control unit 5177 generates a control signal on the basis of the input by the user. Alternatively, where the endoscope 5115 has an AE function, an AF function and an AWB function incorporated therein, the control unit 5177 suitably calculates an optimum exposure value, focal distance and white balance in response to a result of a detection process by the image processing unit 5175 and generates a control signal.

Further, the control unit 5177 controls the display apparatus 5155 to display an image of a surgical region on the basis of an image signal for which the image processes have been performed by the image processing unit 5175. Thereupon, the control unit 5177 recognizes various objects in the surgical region image using various image recognition technologies. For example, the control unit 5177 can recognize a surgical tool such as forceps, a particular living body region, bleeding, mist when the energy device 5135 is used and so forth by detecting the shape, color and so forth of edges of the objects included in the surgical region image. The control unit 5177 causes, when it controls the display apparatus 5155 to display a surgical region image, various kinds of surgery supporting information to be displayed in an overlapping manner with an image of the surgical region using a result of the recognition. Where surgery supporting information is displayed in an overlapping manner and presented to the surgeon 5181, the surgeon 5181 can proceed with the surgery more safety and certainty.

The transmission cable 5179 which connects the camera head 5119 and the CCU 5153 to each other is an electric signal cable ready for communication of an electric signal, an optical fiber ready for optical communication or a composite cable thereof.

Here, while, in the example depicted in the figure, communication is performed by wired communication using the transmission cable 5179, the communication between the camera head 5119 and the CCU 5153 may be performed otherwise by wireless communication. Where the communication between the camera head 5119 and the CCU 5153 is performed by wireless communication, there is no necessity to lay the transmission cable 5179 in the operating room. Therefore, such a situation that movement of medical staff in the operating room is disturbed by the transmission cable 5179 can be eliminated.

An example of the operating room system 5100 to which the technology according to an embodiment of the present disclosure can be applied has been described above. It is to be noted here that, although a case in which the medical system to which the operating room system 5100 is applied is the endoscopic surgery system 5113 has been described as an example, the configuration of the operating room system 5100 is not limited to that of the example described above. For example, the operating room system 5100 may be applied to a soft endoscopic system for inspection or a microscopic surgery system in place of the endoscopic surgery system 5113.

The technology according to the present disclosure is suitably applicable to a display unit constituting the operation room system as a unit displaying a surgical region in the configuration described above. In this case, the surgical region corresponds to a recommended range (a range corresponding to a recommended viewpoint). When the technology according to the present disclosure is applied to the display unit displaying the surgical region, the user is also allowed to appropriately check the surgical region without an obstacle to the visual field while checking other diseased parts and surrounding situations. Moreover, the technology according to the present disclosure is applicable to not only input to an HMD during an operation, for example, but also content used after the operation. For example, the technology according to the present disclosure is applicable to an operation video captured as teaching material content for medical treatments while designating the operation video as a recommended viewpoint (surgical portion, surgeon viewpoint).

3. Modification

Figure 13:
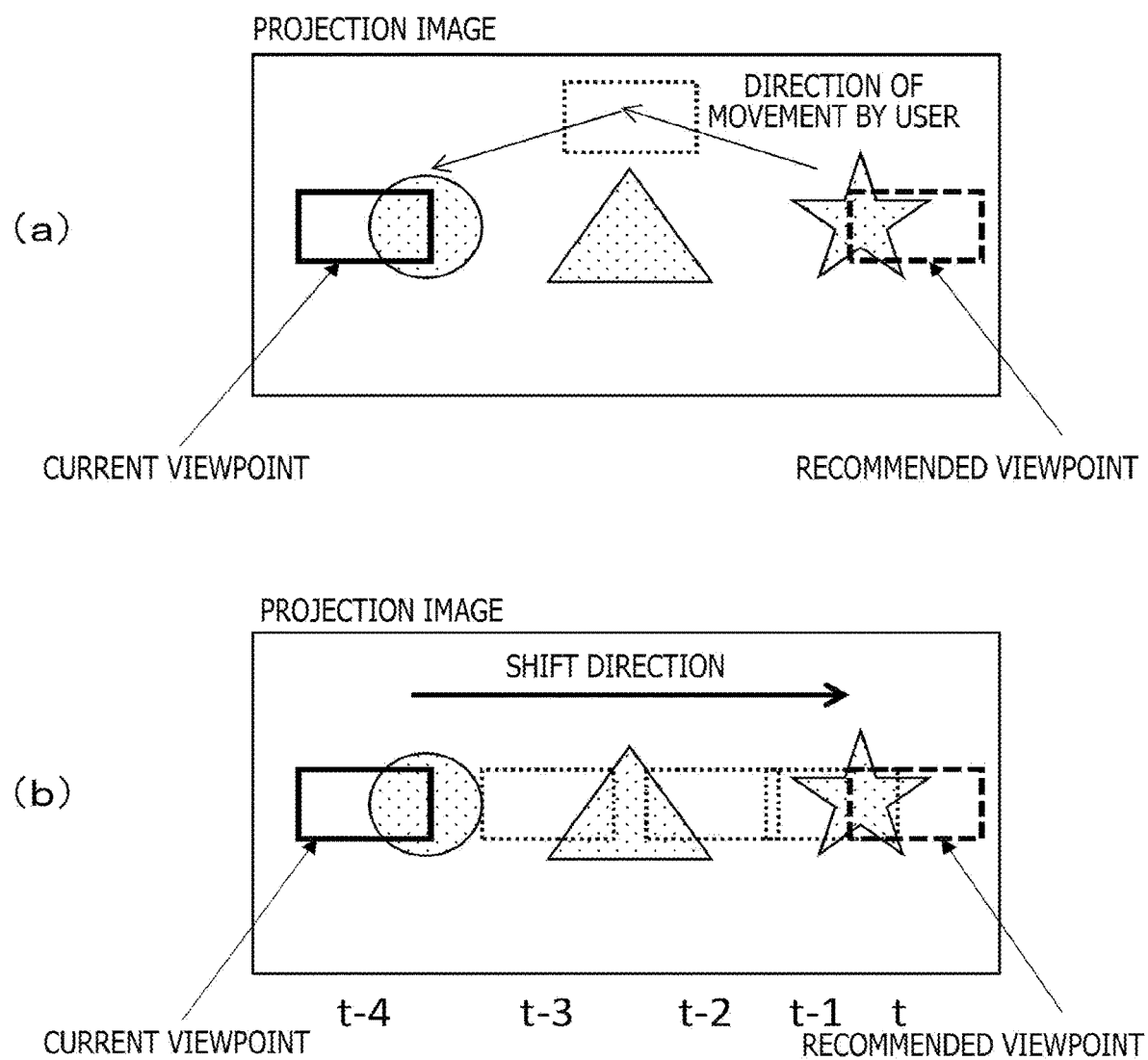
FIG. 13 is a diagram for explaining an example where a current viewpoint is shifted in a direction corresponding to a shortest distance to a recommended viewpoint at the time of transition from a current viewpoint to a recommended viewpoint.

While described in the above embodiment has been the example where a current viewpoint is shifted in a direction opposite to a direction of movement by the user to approach a recommended viewpoint, it may also be considered to shift the current viewpoint in a direction corresponding to a shortest distance to the recommended viewpoint. For example, in a case where a current viewpoint is present at a position deviating from a recommended viewpoint by a curved viewpoint shift caused by a user operation as depicted in FIG. 13(*a*), the current viewpoint may be linearly shifted toward the recommended viewpoint as depicted in FIG. 13(*b*).

Moreover, while described in the above embodiment has been the example where a current viewpoint is shifted in a direction opposite to a direction of movement by the user to approach a recommended viewpoint, it may be considered to shift the current viewpoint along a route not passing through a masked range in a case where the masked range has been set for a shift route. In this case, masked range information may be added to a video stream beforehand together with recommended viewpoint information, for example.

While not described above, it may also be considered that the display device 200 temporarily accumulates a received video stream in a storage, and reads the video stream from the storage and uses the video stream at any subsequent timing. In such a case, it is also possible to set a masked range on the display device 200 side by a user operation.

For example, in a case where a masked range is present in a direction opposite to a direction of movement by the user as depicted in FIG. 14(*a*), a current viewpoint is not shifted in that direction approaching a recommended viewpoint. In FIG. 14(*a*) referred to herein, a broken-line arrow indicates a shift direction in a case of absence of a masked range. In this case, as depicted in FIG. 14(*b*), a route not passing through the masked range is obtained, and the current viewpoint is shifted to approach the recommended viewpoint along the obtained route. The example depicted in the figure indicates an example where a current viewpoint of a t−2 frame returns to a recommended viewpoint of a t frame by two frames. Note that the shift route of the example depicted in the figure is presented only by way of example. It may also be considered to present a route which returns in the direction opposite to the shift direction depicted in the figure while avoiding the masked range upward or downward.

Figure 15:
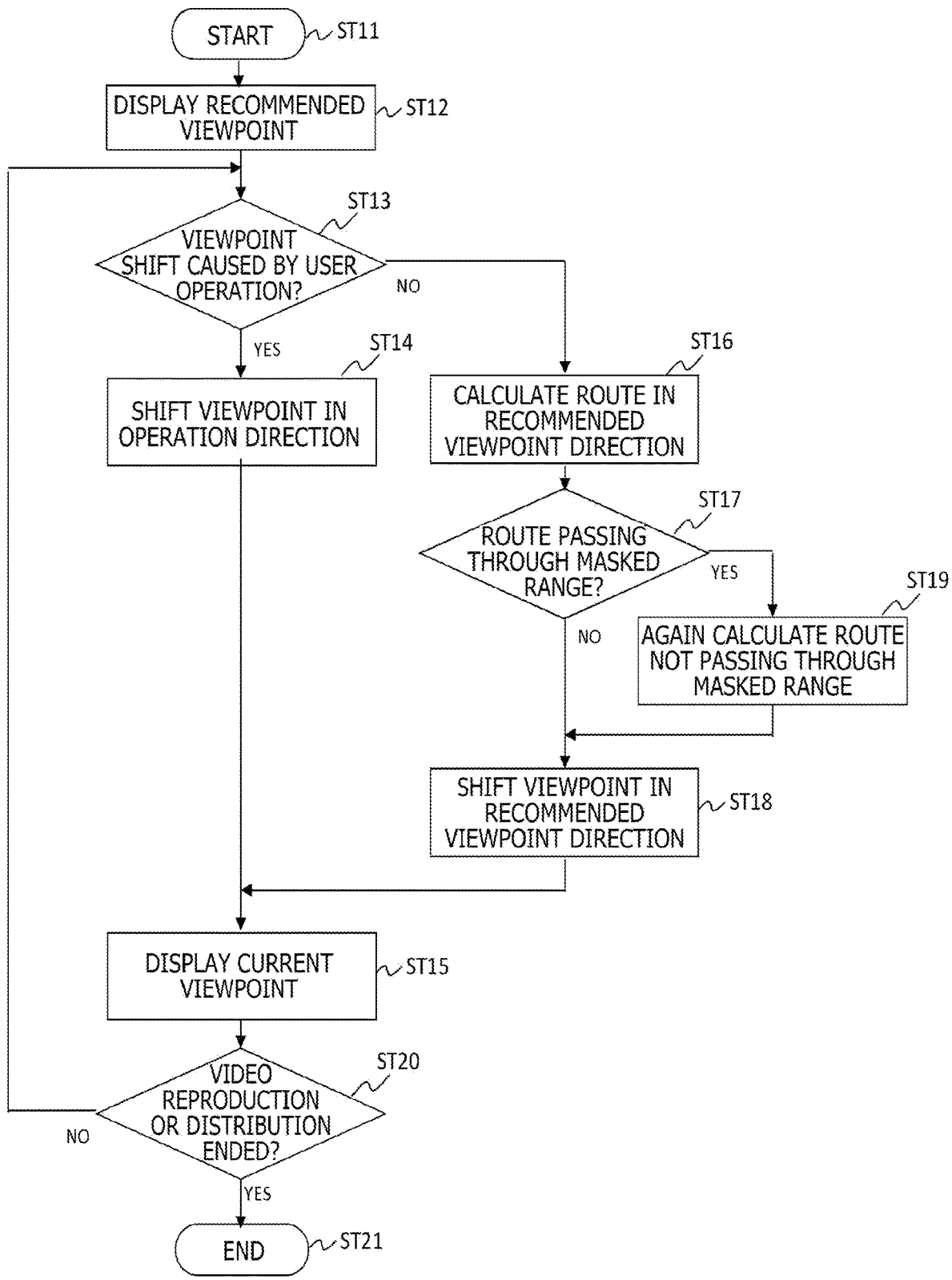
FIG. 15 is a flowchart presenting an example of a display processing procedure performed by the display device in a case of a route not passing through the masked range.

A flowchart presented in FIG. 15 represents an example of a display processing procedure performed by the display device 200 in a case of a route not passing through a masked range.

In step ST11, the display device 200 starts a process in response to a video clip reproduction start operation performed by the user, for example. Subsequently, the display device 200 in step ST12 displays a range corresponding to a recommended viewpoint (recommended range) as an output range. Thereafter, the display device 200 in step ST13 determines whether or not a viewpoint shift has been caused by a user operation.

In a case where a viewpoint shift has been caused by the user, the display device 200 in step ST14 shifts a viewpoint in an operation direction, and then proceeds to processing in step ST15. On the other hand, in a case where no viewpoint shift operation is performed by the user, the display device 200 proceeds to processing in step ST16.

In step ST16, the display device 200 calculates a route in a recommended viewpoint direction. Subsequently, the display device 200 in step ST17 determines whether or not the route passes through the masked range. In a case where the route does not pass through the masked range, the display device 200 proceeds to processing in step ST18. On the other hand, in a case where the route passes through the masked range, the display device 200 in step ST19 again calculates a route not passing through the masked range, and then proceeds to processing in step ST18.

Note that processing in steps ST17 and ST9 is unnecessary if the display device 200 calculates a route not passing through the masked range in step ST16.

In step ST18, the display device 200 shifts the viewpoint in the recommended viewpoint direction along the calculated route, and then proceeds to processing in step S15. In step ST15, the display device 200 displays a range corresponding to a current viewpoint as an output range.

Subsequently, the display device 200 in step ST20 determines whether or not video reproduction or distribution has ended. When it is determined that video reproduction or distribution has not ended yet, the display device 200 returns to processing in step ST13, and reflects a process for a next frame. On the other hand, when it is determined that video reproduction or distribution has ended, a series of processes end in step ST21.

While a case where a masked range lies in a route of a viewpoint shift caused by a user operation is not described above, it may also be considered to pass through a masked range without avoiding the masked range, or calculate a route avoiding a masked range and shift along the calculated route, for example. In addition, in a case where the viewpoint shifts while passing through the masked range, an image in the masked range may be masked, or may be displayed without masking, for example.

Moreover, while described in the above embodiment has been the example where a current viewpoint is shifted in a direction opposite to a direction of movement by the user to approach a recommended viewpoint, it may be considered to shift the current viewpoint along a route not passing through a pass point in a case where the pass point has been set. In this case, pass point information may be added to a video stream beforehand together with recommended viewpoint information, for example.

While not described above, it may also be considered that the display device 200 temporarily accumulates a received video stream in a storage, and reads the video stream from the storage and uses the video stream at any subsequent timing. In such a case, it may also be considered to set a pass point on the display device 200 side by a user operation.

For example, suppose that a pass point is set as depicted in FIG. 16(*a*). In this case, as depicted in FIG. 16(*b*), a route passing through the pass point is obtained, and a current viewpoint is shifted to approach a recommended viewpoint along the route. The example depicted in the figure is an example where a current viewpoint of a t−4 frame returns to a recommended viewpoint of a t frame by four frames.

Figure 17:
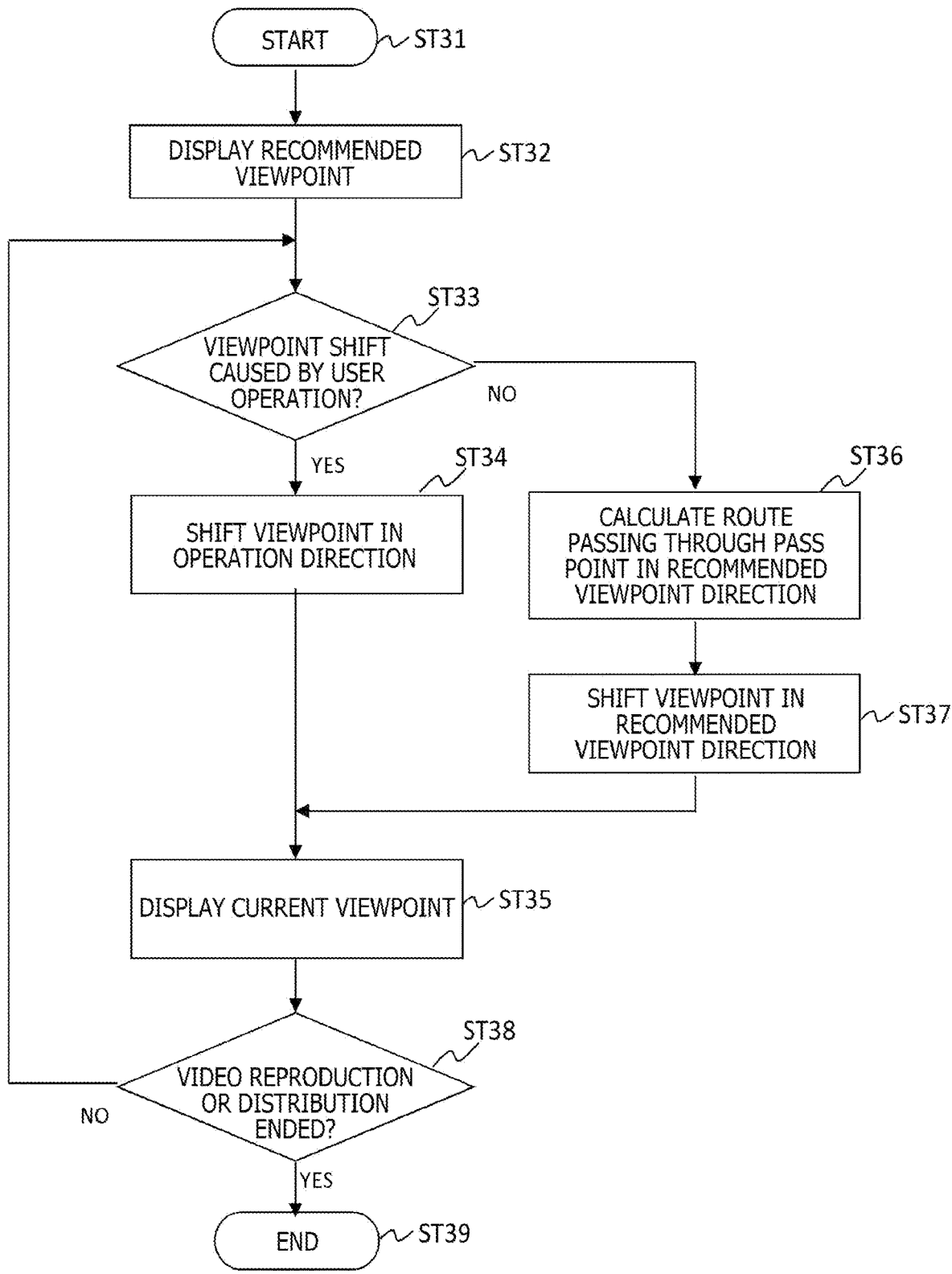
FIG. 17 is a flowchart presenting an example of a display processing procedure performed by the display device in a case of a route passing through a pass point.

A flowchart presented in FIG. 17 represents an example of a display processing procedure performed by the display device 200 in a case of a route passing through a pass point.

In step ST31, the display device 200 starts a process in response to a video clip reproduction start operation performed by the user, for example. Subsequently, the display device 200 in step ST32 displays a range corresponding to a recommended viewpoint (recommended range) as an output range. Thereafter, the display device 200 in step ST33 determines whether or not a viewpoint shift has been caused by a user operation.

In a case where a viewpoint shift has been caused by the user, the display device 200 in step ST34 shifts a viewpoint in an operation direction, and then proceeds to processing in step ST35. On the other hand, in a case where no viewpoint shift operation by the user is performed, the display device 200 proceeds to processing in step ST36.

In step ST36, the display device 200 calculates a route extending in a recommended viewpoint direction and passing through a pass point. Subsequently, the display device 200 in step ST37 shifts the viewpoint in the recommended viewpoint direction along the calculated route, and then proceeds to processing in step ST35. In step ST35, the display device 200 displays a range corresponding to a current viewpoint as an output range.

Subsequently, the display device 200 in step ST38 determines whether or not video reproduction or distribution has ended. When it is determined that video reproduction or distribution has not ended yet, the display device 200 returns to processing in step ST33, and reflects a process for a next frame. On the other hand, when it is determined that video reproduction or distribution has ended, a series of processes end in step ST39.

Furthermore, while the case where the one recommended viewpoint is present has been described in the above embodiment by way of example, there may be such a case where a plurality of recommended viewpoints is present. For example, a plurality of performers may be present within a same image, and positions of the respective performers may be set as recommended viewpoints.

In a case where a plurality of recommended viewpoints is present as described above, it may be considered to shift toward a recommended viewpoint located closest in the plurality of recommended viewpoints or shift toward a recommended viewpoint selected by the user beforehand at the time of return from a current viewpoint to a recommended viewpoint.

Figure 18:
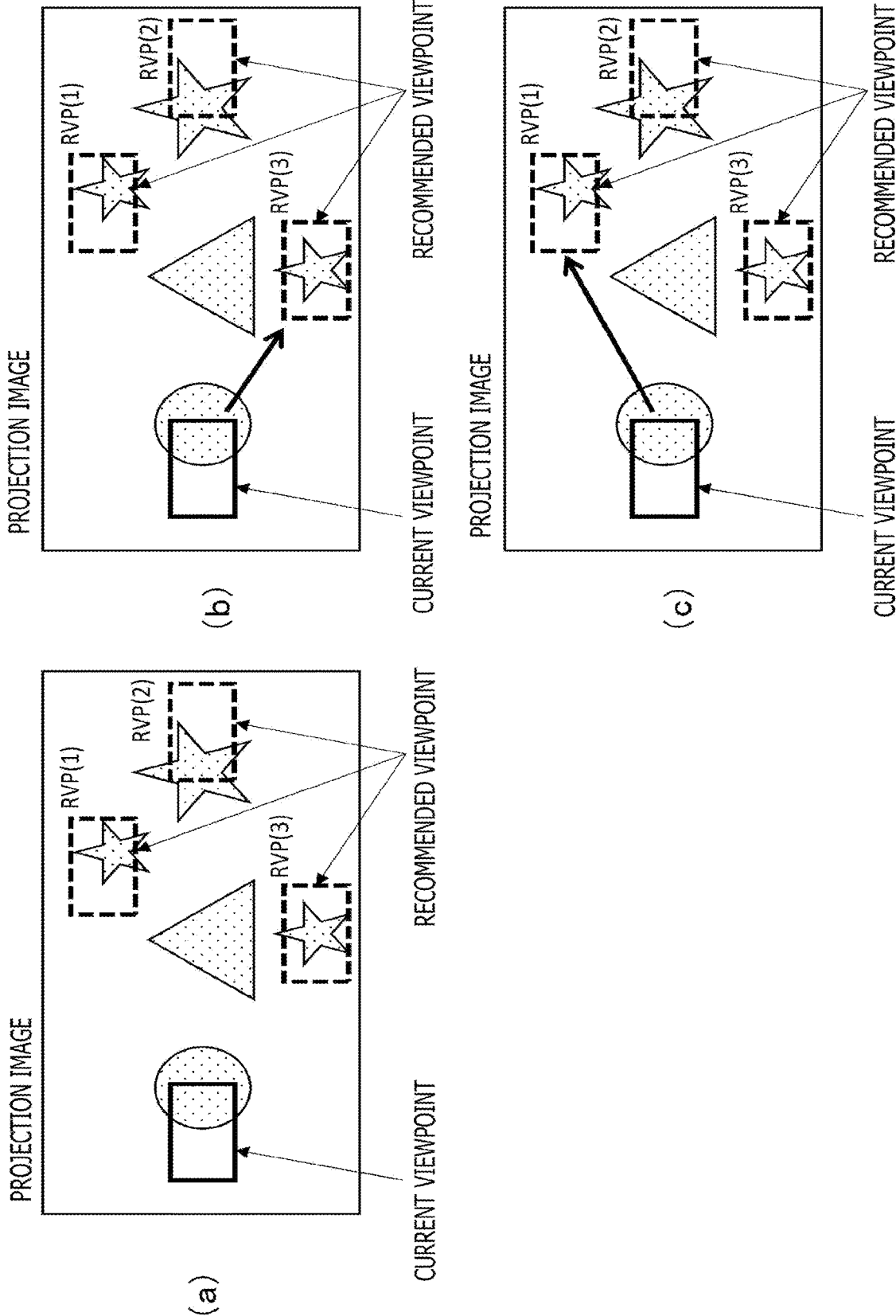
FIG. 18 is a diagram for explaining a case where a plurality of recommended viewpoints is present at the time of transition from a current viewpoint to a recommended viewpoint.

FIG. 18(*a*) depicts an example where a plurality of recommended viewpoints is present. FIG. 18(*b*) depicts an example where a current viewpoint shifts toward a recommended viewpoint located closest in a plurality of recommended viewpoints at the time of return from the current viewpoint to a recommended viewpoint. In this example, a recommended viewpoint RVP(3) is located closest. Accordingly, the current viewpoint shifts toward the recommended viewpoint RVP(3). FIG. 18(*c*) depicts an example where the current viewpoint shifts toward a recommended viewpoint selected by the user in a plurality of recommended viewpoints at the time of return from the current viewpoint to a recommended viewpoint. In this example, a recommended viewpoint RVP(1) is selected by the user. Accordingly, the current viewpoint shifts toward the recommended viewpoint RVP(1).

Figure 19:
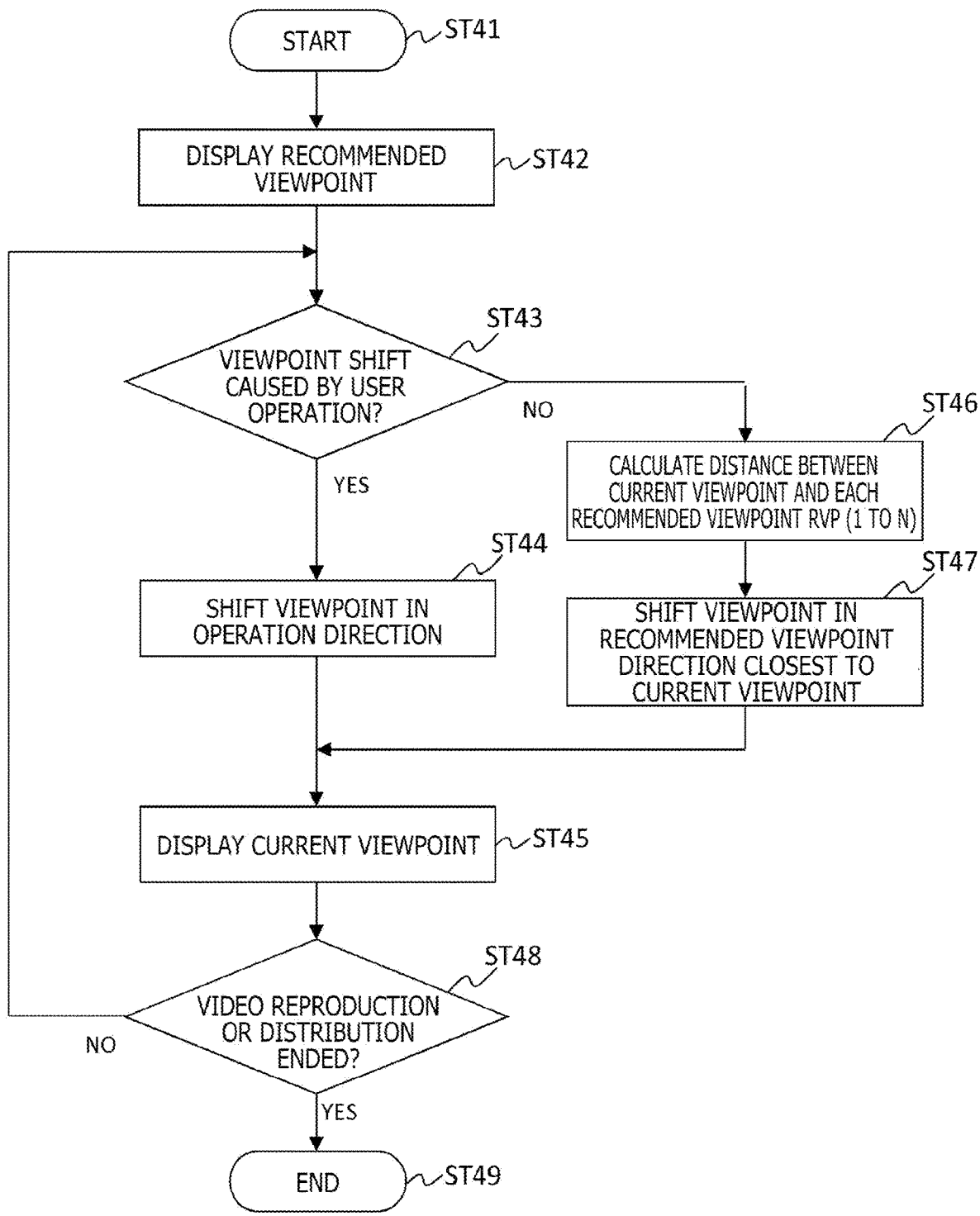
FIG. 19 is a flowchart presenting an example of a display processing procedure performed by the display device in a case where a current viewpoint shifts toward a recommended viewpoint located closest in a plurality of recommended viewpoints.

A flowchart in FIG. 19 presents an example of a display processing procedure performed by the display device 200 in a case where a current viewpoint shifts toward a recommended viewpoint located closest in a plurality of recommended viewpoints.

In step ST41, the display device 200 starts a process in response to a video clip reproduction start operation performed by the user, for example.

Subsequently, the display device 200 in step ST42 displays a range corresponding to a recommended viewpoint (recommended range) as an output range. For example, the recommended viewpoint herein is a recommended viewpoint determined beforehand.

Thereafter, the display device 200 in step ST43 determines whether or not a viewpoint shift has been caused by a user operation. In a case where a viewpoint shift has been caused by the user, the display device 200 in step ST44 shifts the viewpoint in an operation direction, and then proceeds to processing in step ST45.

On the other hand, in a case where no viewpoint shift operation is performed by the user, the display device 200 proceeds to processing in step ST46. In step ST46 herein, the display device 200 calculates a distance between a current viewpoint and each of recommended viewpoints RVP (1 to N).

Thereafter, the display device 200 in step ST47 calculates a route in a recommended viewpoint direction closest to the current viewpoint, shifts the viewpoint in the recommended viewpoint direction along the calculated route, and then proceeds to processing in step ST45. In step ST45, the display device 200 displays a range corresponding to a current viewpoint as an output range.

Subsequently, the display device 200 in step ST48 determines whether or not video reproduction or distribution has ended. When it is determined that video reproduction or distribution has not ended yet, the display device 200 returns to processing in step ST43, and reflects a process for a next frame. On the other hand, when it is determined that video reproduction or distribution has ended, a series of processes end in step ST49.

Figure 20:
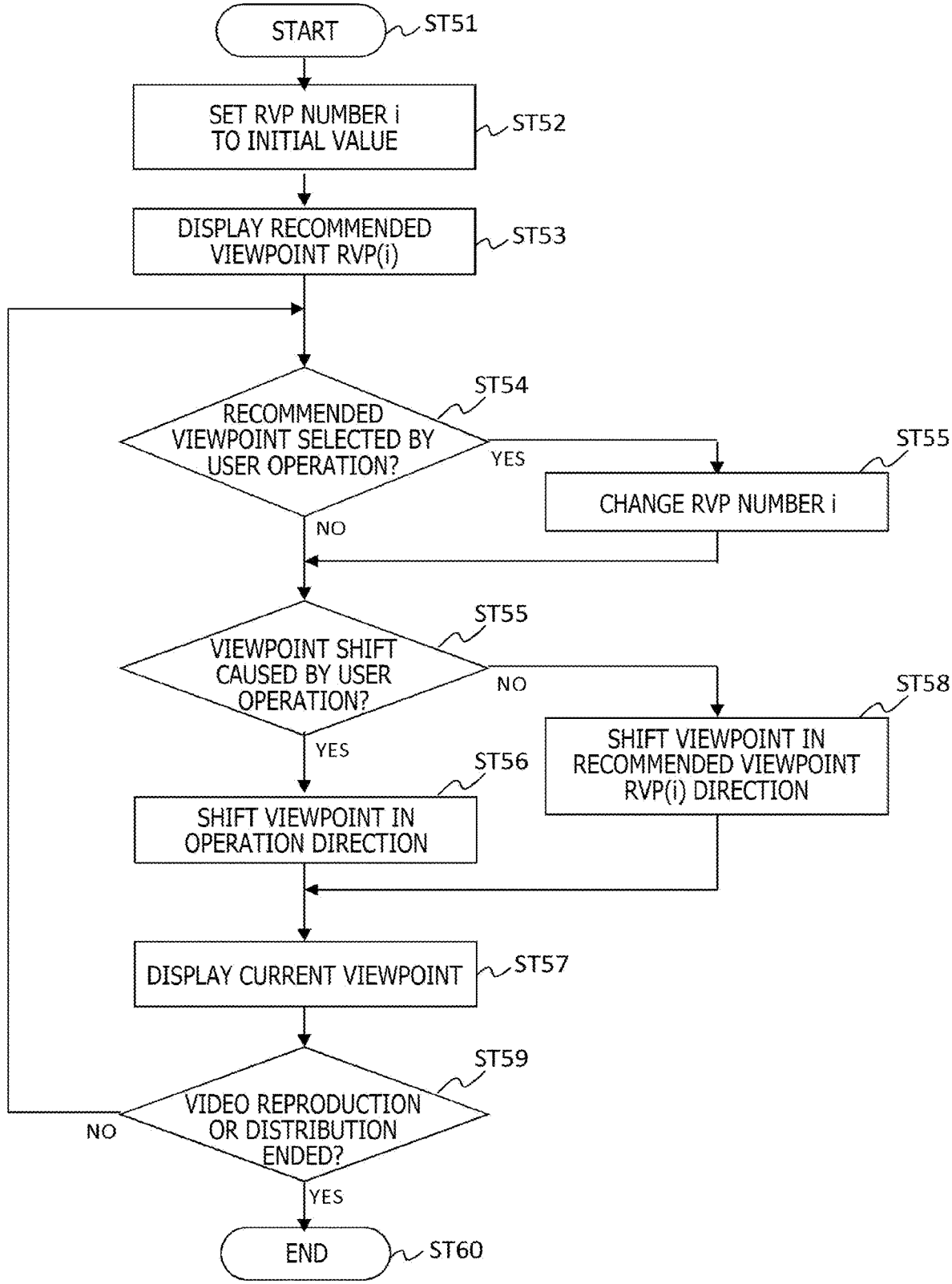
FIG. 20 is a flowchart presenting an example of a display processing procedure performed by the display device in a case of a shift toward a recommended viewpoint selected by the user in a plurality of recommended viewpoints.

A flowchart in FIG. 20 presents an example of a display processing procedure performed by the display device 200 in a case of a shift toward a recommended viewpoint selected by the user in a plurality of recommended viewpoints.

In step ST51, the display device 200 starts a process in response to a video clip reproduction start operation performed by the user, for example.

Subsequently, the display device 200 in step ST52 sets a recommended viewpoint number (RVP number) i to an initial value such as "1." Thereafter, the display device 200 in step ST53 displays a range corresponding to the recommended viewpoint RVP(i) (recommended range) as an output range.

Then, the display device 200 in step ST54 determines whether or not a recommended viewpoint has been selected by a user operation. In a case where no recommended viewpoint has been selected by a user operation, the display device 200 immediately proceeds to processing in step ST55. On the other hand, when it is determined that a recommended viewpoint has been selected by a user operation, the display device 200 in step ST55 changes the recommended viewpoint number (RVP number) i to a number selected by the user, and then proceeds to processing in step ST55.

Thereafter, the display device 200 in step ST55 determines whether or not a viewpoint shift has been caused by a user operation. In a case where a viewpoint shift has been caused by the user, the display device 200 in step ST56 shifts the viewpoint in an operation direction, and then proceeds to processing in step ST57.

On the other hand, in a case where no viewpoint shift operation is caused by the user, the display device 200 in step ST58 calculates a route in a direction toward the recommended viewpoint RVP(i), shifts the viewpoint in the recommended viewpoint direction along the calculated route, and then proceeds to processing in step ST57. In step ST57, the display device 200 displays a range corresponding to a current viewpoint as an output range.

Subsequently, the display device 200 in step ST59 determines whether or not video reproduction or distribution has ended. When it is determined that video reproduction or distribution has not ended yet, the display device 200 returns to processing in step ST54, and reflects a process for a next frame. On the other hand, when it is determined that video reproduction or distribution has ended, a series of processes end in step ST60.

Moreover, described in the above embodiment has been the example where a current viewpoint is shifted in a recommended viewpoint direction on the basis of a condition that the current viewpoint (output range) deviates from the recommended viewpoint (recommended range), i.e., the current viewpoint is different from the recommended viewpoint.

Figure 21:
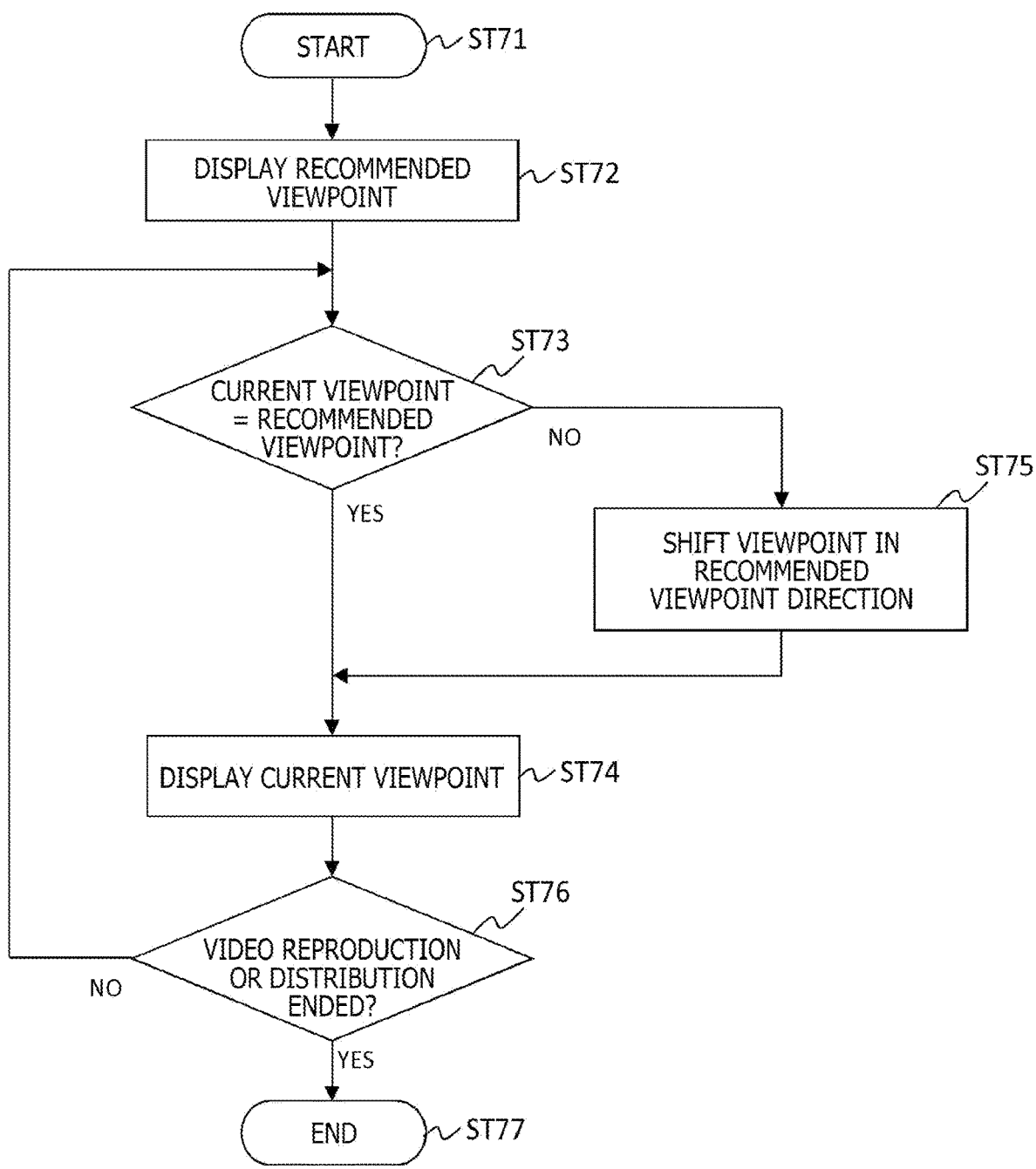
FIG. 21 is a flowchart presenting an example of a display processing procedure performed by the display device in a case of a shift toward a recommended viewpoint on the basis of whether or not a recommended viewpoint has been indicated.

A flowchart in FIG. 21 presents an example of a display processing procedure performed by the display device 200 in a case of a shift toward a recommended viewpoint on the basis of whether or not a recommended viewpoint has been displayed. In step ST71, the display device 200 starts a process in response to a video clip reproduction start operation performed by the user, for example.

Subsequently, the display device 200 in step ST72 displays a range corresponding to a recommended viewpoint (recommended range) as an output range. Then, the display device 200 in step ST73 determines whether or not a current viewpoint is a recommended viewpoint.

In a case where the current viewpoint is the recommended viewpoint, the display device 200 proceeds to processing in step ST74. On the other hand, in a case where the current viewpoint is not the recommended viewpoint, the display device 200 in step ST75 calculates a route in a recommended viewpoint direction, shifts the viewpoint in the recommended viewpoint direction along the calculated route, and then proceeds to processing in step ST74. In step ST74, the display device 200 displays a range corresponding to the current viewpoint as an output range.

Subsequently, the display device 200 in step ST76 determines whether or not video reproduction or distribution has ended. When it is determined that video reproduction or distribution has not ended yet, the display device 200 returns to processing in step ST73, and reflects a process for a next frame. On the other hand, when it is determined that video reproduction or distribution has ended, a series of processes end in step ST77.

Note that the recommended viewpoint is displayed in step S72, and that whether or not the current viewpoint is the recommended viewpoint is determined in step ST73 in the flowchart in FIG. 21. These are performed on an assumption that there may occur such a case where the current viewpoint is shifted from the recommended viewpoint and located at a position different from the recommended viewpoint on the basis of the fact that the time (frame) in step ST73 includes the time (frame) having advanced from step ST72. Possible examples of the case where the current viewpoint is different from the recommended viewpoint include a case where the viewpoint has been changed by the user in a frame before the current frame.

Moreover, each of following conditions may be considered as a condition for shifting the current viewpoint in a recommended viewpoint direction.

For example, considered may be such a condition where a predetermined time has elapsed in a state of deviation of a current viewpoint from a recommended viewpoint, i.e., in a state where a current viewpoint is different from a recommended viewpoint.

Figure 22:
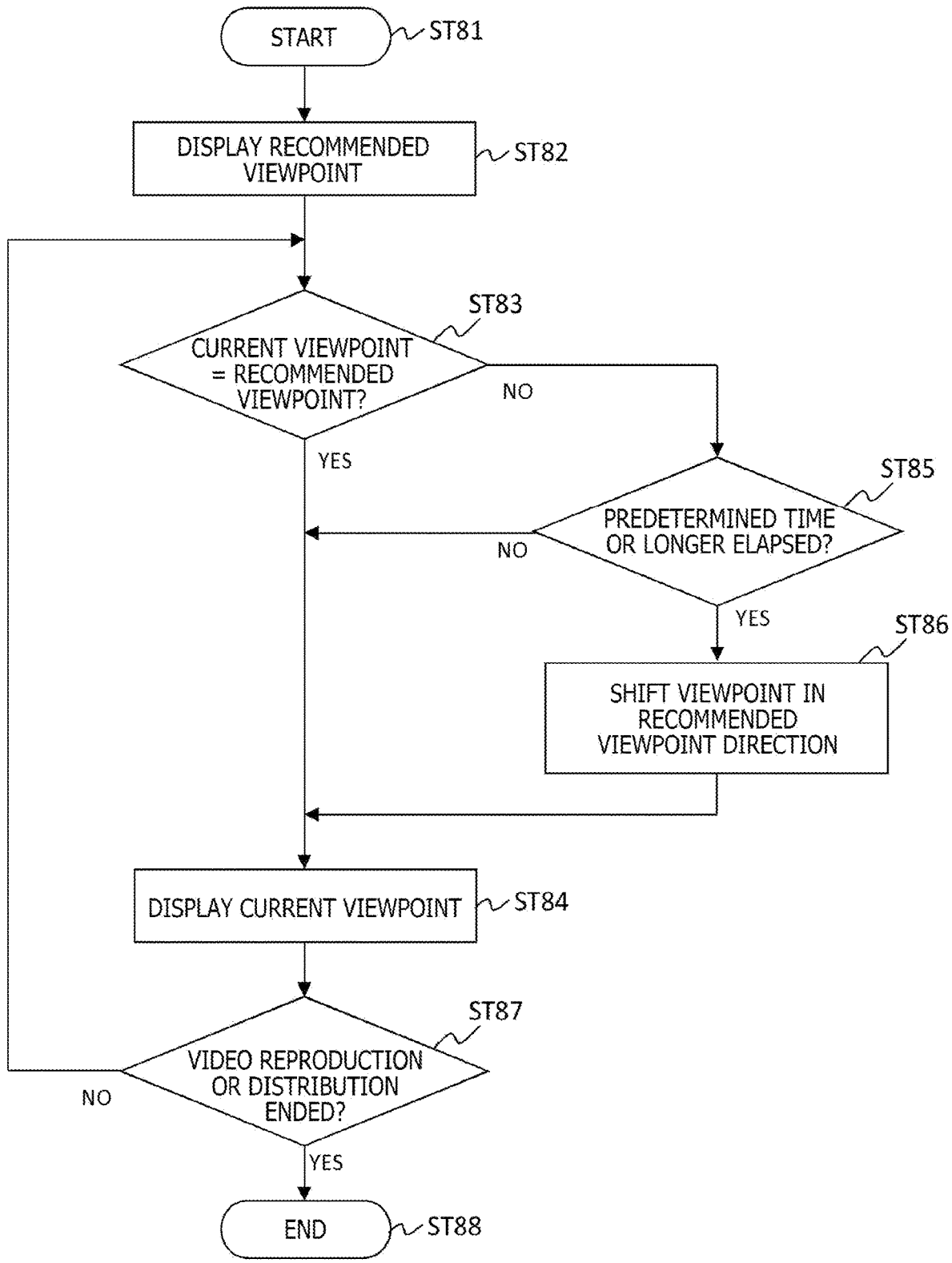
FIG. 22 is a flowchart presenting an example of a display processing procedure performed by the display device in a case of a shift toward a recommended viewpoint without recommended viewpoint display on the basis of whether or not a predetermined time or longer has elapsed.

A flowchart in FIG. 22 presents an example of a display processing procedure performed by the display device 200 in a case of a shift toward a recommended viewpoint on the basis of whether or not a predetermined time has elapsed without display of the recommended viewpoint. In step ST81, the display device 200 starts a process in response to a video clip reproduction start operation performed by the user, for example.

Subsequently, the display device 200 in step ST82 displays a range corresponding to a recommended viewpoint (recommended range) as an output range. Then, the display device 200 in step ST83 determines whether or not a current viewpoint is a recommended viewpoint. In a case where the current viewpoint is the recommended viewpoint, the display device 200 proceeds to processing in step ST84.

On the other hand, in a case where the current viewpoint is not the recommended viewpoint, the display device 200 in step ST85 determines whether or not a predetermined time or longer has elapsed in a state where the current viewpoint is not the recommended viewpoint. The predetermined time can be set beforehand, or can be changed to any time by the user. In a case where the predetermined time or longer has not elapsed yet, the display device 200 proceeds to step ST84. On the other hand, in a case where the predetermined time or longer has elapsed, the display device 200 in step ST86 calculates a route in a recommended viewpoint direction, shifts the viewpoint in the recommended viewpoint direction along the calculated route, and then proceeds to processing in step ST84.

In step ST84, the display device 200 displays a range corresponding to a current viewpoint as an output range. Subsequently, the display device 200 in step ST87 determines whether or not video reproduction or distribution has ended. When it is determined that video reproduction or distribution has not ended yet, the display device 200 returns to processing in step ST83, and reflects a process for a next frame. On the other hand, when it is determined that video reproduction or distribution has ended, a series of processes end in step ST88.

Moreover, for example, considered as a shift condition may be such a case where a viewpoint position change instruction issued by a user operation has not been detected. Furthermore, for example, considered as a shift condition may be such a case where a current viewpoint lies within a specific range in an image. The specific range herein is an image region in a rear surface direction, for example.

In addition, for example, considered as a shift condition may be such a case where an output range deviates from a recommended range in a state where an image is contained in an image of a specific frame. In this case, whether or not the image is contained in the image of the specific frame may be added to a video stream beforehand together with recommended viewpoint information, for example. Besides, for example, considered as a shift condition may be such a case where an instruction of transition to a recommended viewpoint has been issued by the user in a state where a current viewpoint deviates from the recommended viewpoint.

A flowchart presented in FIG. 23 represents an example of a display processing procedure performed by the display device 200. In step ST101, the display device 200 starts a process in response to a video clip reproduction start operation performed by the user, for example.

Subsequently, the display device 200 in step ST102 displays a range corresponding to a recommended viewpoint (recommended range) as an output range. Then, the display device 200 in step ST103 determines whether or not a current viewpoint is a recommended viewpoint. In a case where the current viewpoint is the recommended viewpoint, the display device 200 proceeds to processing in step ST111.

On the other hand, in a case where the current viewpoint is not the recommended viewpoint, the display device 200 in step ST104 determines whether or not a predetermined time has elapsed. In a case where the predetermined time has not elapsed yet, the display device 200 in step ST105 determines whether or not a viewpoint shift has been caused by a user operation. In a case where a viewpoint shift has been caused, the display device 200 in step ST106 determines whether or not a viewpoint position after the shift is located at a specific position.

This determination is made not after an actual shift, but is made to determine whether or not the shift destination is located at the specific position at the time of reception of the user operation. Examples of the specific position include a position corresponding to a rear surface of the recommended viewpoint, and a position at a certain distance or longer from the recommended viewpoint, for example.

In a case where the viewpoint position after the shift is not the specific position, the display device 200 in step ST107 determines whether or not the viewpoint position is contained in a specific frame. In a case where the viewpoint position is not contained in the specific frame, the display device 200 in step ST108 shifts the viewpoint in an operation direction, and then proceeds to processing in step ST109.

In a case where the predetermined time has elapsed in step ST104, in a case where a viewpoint shift has not been caused in step ST105, in a case where the viewpoint position after the shift is the specific position in step ST106, or in a case where the viewpoint position is contained in the specific frame in step ST107, the display device 200 in step ST110 calculates a route in a recommended viewpoint direction, shifts the viewpoint in the recommended viewpoint direction along the calculated route, and then proceeds to processing in step ST109. In step ST109, the display device 200 displays a range corresponding to a current viewpoint as an output range.

Subsequently, the display device 200 in step ST111 determines whether or not video reproduction or distribution has ended. When it is determined that video reproduction or distribution has not ended yet, the display device 200 returns to processing in step ST103, and reflects a process for a next frame. On the other hand, when it is determined that video reproduction or distribution has ended, a series of processes end in step ST112.

Moreover, described in the above embodiment has been the case where speed control is performed such that the approach speed increases as a positional difference between a current viewpoint and a recommended viewpoint increases, and that the approach speed decreases as this positional difference decreases. In other words, the transition speed is made higher in a case of a larger positional difference than in a case of a smaller positional difference. However, for example, it may be considered to perform speed control in such a manner as to return to a recommended viewpoint within a certain time. Moreover, for example, it may also be considered to perform speed control in such a manner as to return to a recommended viewpoint at a certain speed.

Furthermore, while a route for transitioning from a current viewpoint to a recommended viewpoint is interpolated by spherical linear interpolation in the embodiment described above, it may be considered to interpolate this transition route by linear interpolation.

In addition, described in the above embodiment has been the case where a current viewpoint is shifted so as to gradually approach a recommended viewpoint at the time of transition from the current viewpoint to the recommended viewpoint. However, it may be considered to instantaneously shift the current viewpoint to the recommended viewpoint at the time of this transition.

Moreover, while described in the above embodiment has been the example handling a VR image as a wide viewing angle image, an example handling a panorama image may be similarly considered. Furthermore, while described in the above embodiment has been the example handling a two-dimensional image, an example handling a three-dimensional image may be similarly considered.

In addition, while the preferred embodiment of the present disclosure has been described in detail with reference to the accompanying drawings, the technical scope of the present disclosure is not limited to this example. It is apparent for those having ordinary knowledges in the technical field of the present disclosure that various examples of modifications and corrections can occur within the scope of the technical spirit described in the claims. Needless to say, it is understood that these modifications and corrections also belong to the technical scope of the present disclosure.

Moreover, advantageous effects described in the present description are presented merely for giving explanation or examples, and not as limited advantageous effects. Accordingly, the technology according to the present disclosure can offer other advantageous effects apparent for those skilled in the art in the light of the present description in addition to or in place of the advantageous effects described above.

In addition, the present technology may have following configurations.

(1) An image processing apparatus including:
  a detection unit that detects viewpoint shift information according to a viewpoint position change instruction;
  an output range determination unit that determines an output range of an image containing recommended viewpoint information on the basis of the recommended viewpoint information and the viewpoint shift information; and
  an output unit that outputs a part of the image to a display unit as a display image on the basis of the determined output range,
  in which the output range determination unit determines the output range such that the display image lies within a recommended range indicated by the recommended viewpoint information in a case where the display image meets a predetermined condition.

(2) The image processing apparatus according to (1) described above, in which the output range determination unit determines the output range such that the display image transits in a direction toward the recommended range.

(3) The image processing apparatus according to (1) or (2) described above, in which the predetermined condition includes a case where the display image is different from the recommended range.

(4) The image processing apparatus according to (1) or (2) described above, in which the predetermined condition includes a case where the display image is different from the recommended range for a predetermined time or longer.

(5) The image processing apparatus according to (3) described above, in which the predetermined condition additionally includes a case where the viewpoint shift information is not detected.

(6) The image processing apparatus according to (1) or (2) described above, in which the predetermined condition includes a case where the display image lies within a specific range in the image.

(7) The image processing apparatus according to (1) or (2) described above, in which the predetermined condition includes a case where the display image is different from the recommended range in a state where the image is contained in an image of a specific frame.

(8) The image processing apparatus according to (1) or (2) described above, in which the predetermined condition includes a case where the display image is different from the recommended range and besides an instruction of transition to the recommended range is issued as the viewpoint shift information.

(9) The image processing apparatus according to any one of (2) to (8) described above, in which the output range determination unit controls a speed of the transition on the basis of a positional difference between the display image and the recommended range such that the speed of the transition becomes higher in a case where the positional difference is large than in a case where the positional difference is small.

(10) The image processing apparatus according to any one of (2) to (8) described above, in which the output range determination unit controls a speed of the transition such that return to the recommended range is achieved within a certain time.

(11) The image processing apparatus according to any one of (2) to (8) described above, in which the output range determination unit controls a speed of the transition such that return to the recommended range is achieved at a certain speed.

(12) The image processing apparatus according to any one of (2) to (11) described above, in which the output range determination unit interpolates a route of the transition by spherical linear interpolation.

(13) The image processing apparatus according to any one of (2) to (11) described above, in which the output range determination unit interpolates a route of the transition by linear interpolation.

(14) The image processing apparatus according to any one of (2) to (13) described above, in which, in a case where the display image is different from the recommended range as a result of a change of a viewpoint position based on the viewpoint shift information, the output range determination unit determines the output range such that a shift is achieved along a route in a direction opposite to a viewpoint position change direction corresponding to the change of the viewpoint position at the time of the transition.

(15) The image processing apparatus according to any one of (2) to (13) described above, in which the output range determination unit determines the output range such that a shift is achieved along a shortest route to the recommended range from the display image at the time of the transition.

(16) The image processing apparatus according to any one of (2) to (15) described above, in which, in a case where the image contains masked range information indicating a masked range, the output range determination unit determines the output range such that a shift is achieved along a route not passing through the masked range at the time of the transition.

(17) The image processing apparatus according to any one of (2) to (16) described above, in which, in a case where the image contains pass point information indicating a pass point, the output range determination unit determines the output range such that a shift is achieved along a route passing through the pass point at the time of the transition.

(18) The image processing apparatus according to any one of (1) to (17) described above, in which, in a case where the recommended viewpoint information contains a plurality of recommended ranges, the output range determination unit determines the output range such that a shift is achieved toward a recommended range located at a position closest to the display image in the plurality of recommended ranges, or toward a recommended range located at a position selected by a user at the time of the transition.

(19) An image processing method including:
a procedure for detecting viewpoint shift information according to a viewpoint position change instruction;
a procedure for determining an output range of an image containing recommended viewpoint information on the basis of the recommended viewpoint information and the viewpoint shift information; and
a procedure for outputting a part of the image to a display unit as a display image on the basis of the determined output range,
in which, in the procedure for determining the output range, the output range is determined such that the display image lies within a recommended range indicated by the recommended viewpoint information in a case where the display image meets a predetermined condition.

(20) A program that causes a computer to function as:
detection means that detects viewpoint shift information according to a viewpoint position change instruction;
output range determination means that determines an output range of an image containing recommended viewpoint information on the basis of the recommended viewpoint information and the viewpoint shift information; and
output means that outputs a part of the image to a display unit as a display image on the basis of the determined output range,
in which the output range determination means determines the output range such that the display image lies within a recommended viewpoint range indicated by the recommended viewpoint information in a case where the display image meets a predetermined condition.

REFERENCE SIGNS LIST

10: Image distribution system
101: Multicamera

102: Wide viewing angle image conversion unit
103: Encoder
104: Distribution server
200: Display device
201: Reception unit
202: Decoder
203: Visual field drawing unit
204: Gyro sensor
205: Viewpoint shift information calculation unit
206: Transition calculation unit
207: Display unit

The invention claimed is:

1. An image processing apparatus, comprising:
processing circuitry configured to
 display a current image using a current viewpoint;
 decode, from a received video stream, recommended viewpoint information for a next frame and image data of an image for the next frame, the recommended viewpoint information including position and angle information defining at least one recommended viewpoint for the next frame;
 detect viewpoint shift information according to a viewpoint position change instruction input by a user operation, the viewpoint shift information indicating a shift direction;
 determine an output range of the image for the next frame based on (1) the decoded recommended viewpoint information associated with the image, (2) the detected viewpoint shift information, the recommended viewpoint information being separate and independent of the viewpoint shift information input by the user operation, and (3) the current viewpoint; and
 output a part of the image to a display as a display image based on the determined output range,
 wherein, when the recommended viewpoint information contains a plurality of recommended viewpoints, the processing circuitry is further configured to determine the output range such that a shift is achieved toward a first recommended viewpoint, of the plurality of recommended viewpoints, located at a position closest in distance to the current viewpoint.

2. The image processing apparatus according to claim 1, wherein the processing circuitry is further configured to determine the output range so that the display image shifts based on the recommended range when the display image is different from the recommended range.

3. The image processing apparatus according to claim 1, wherein the processing circuitry is further configured to determine the output range so that the display image shifts based on the recommended range when the display image is different from the recommended range for a predetermined time or longer.

4. The image processing apparatus according to claim 1, wherein the processing circuitry is further configured to determine the output range so that the display image shifts based on the recommended range when the display image lies within a specific range in the image.

5. The image processing apparatus according to claim 1, wherein the processing circuitry is further configured to determine the output range so that the display image shifts based on the recommended range when the display image is different from the recommended range in a state where the image is contained in an image of a specific frame.

6. The image processing apparatus according to claim 1, wherein the processing circuitry is further configured to determine the output range so that the display image shifts based on the recommended range when the display image is different from the recommended range and an instruction of transition to the recommended range is issued as the viewpoint shift information.

7. The image processing apparatus of claim 1, wherein, when the image contains masked range information indicating a masked range, the processing circuitry is further configured to determine the output range such that a shift is achieved along a route not passing through the masked range at a time of the shift.

8. The image processing apparatus according to claim 1, wherein the processing circuitry is further configured to determine the output range such that the display image transits in a direction toward the recommended range.

9. The image processing apparatus according to claim 8, wherein the processing circuitry is further configured to control a speed of the transition based on a positional difference between the display image and the recommended range such that the speed of the transition becomes higher as the positional difference is larger.

10. The image processing apparatus according to claim 8, wherein the processing circuitry is further configured to control a speed of the transition such that a return to the recommended range is achieved within a certain time.

11. The image processing apparatus according to claim 8, wherein the processing circuitry is further configured to control a speed of the transition such that return to the recommended range is achieved at a certain speed.

12. The image processing apparatus according to claim 8, wherein the processing circuitry is further configured to interpolate a route of the transition by spherical linear interpolation.

13. The image processing apparatus according to claim 8, wherein the processing circuitry is further configured to interpolate a route of the transition by linear interpolation.

14. The image processing apparatus according to claim 8, wherein, when the display image is different from the recommended range as a result of a change of a viewpoint position based on the viewpoint shift information, the processing circuitry is further configured to determine the output range such that a shift is achieved along a route in a direction opposite to a viewpoint position change direction corresponding to the change of the viewpoint position at a time of the transition.

15. The image processing apparatus according to claim 8, wherein the processing circuitry is further configured to determine the output range such that a shift is achieved along a shortest route to the recommended range from the display image at a time of the transition.

16. The image processing apparatus according to claim 8, wherein, when the image contains pass point information indicating a pass point, the processing circuitry is further configured to determine the output range such that a shift is achieved along a route passing through the pass point at a time of the transition.

17. An image processing method, comprising:
 displaying a current image using a current viewpoint;
 decoding, from a received video stream, recommended viewpoint information for a next frame and image data of an image for the next frame, the recommended viewpoint information including position and angle information defining at least one recommended viewpoint for the next frame;

detecting viewpoint shift information according to a viewpoint position change instruction input by a user operation, the viewpoint shift information indicating a shift direction;

determine an output range of the image for the next frame based on (1) the decoded recommended viewpoint information associated with the image, (2) the detected viewpoint shift information, the recommended viewpoint information being separate and independent of the viewpoint shift information input by the user operation, and (3) the current viewpoint; and outputting a part of the image to a display as a display image based on the determined output range, wherein the recommended viewpoint information contains a plurality of recommended viewpoints and the determining step further comprises determining the output range such that a shift is achieved toward a first recommended viewpoint, of the plurality of recommended viewpoints, located at a position closest in distance to the current viewpoint.

18. A non-transitory computer-readable medium storing a program that, when executed by a computer, causes the computer to perform a method comprising:

displaying a current image using a current viewpoint;

decoding, from a received video stream, recommended viewpoint information for a next frame and image data of an image for the next frame, the recommended viewpoint information including position and angle information defining at least one recommended viewpoint for the next frame;

detecting viewpoint shift information according to a viewpoint position change instruction input by a user operation, the viewpoint shift information indicating a shift direction;

determining an output range of the image for the next frame based on (1) the detected recommended viewpoint information associated with the image, (2) the detected viewpoint shift information, the recommended viewpoint information being separate and independent of the viewpoint shift information input by the user operation, and (3) the current viewpoint; and outputting a part of the image to a display as a display image based on the determined output range, wherein, when the recommended viewpoint information contains a plurality of recommended viewpoints, the determining step further comprises determining the output range such that a shift is achieved toward a first recommended viewpoint, of the plurality of recommended viewpoints, located at a position closest in distance to the current viewpoint.

* * * * *